United States Patent [19]
Laqueyrerie et al.

[11] Patent Number: 5,866,130
[45] Date of Patent: Feb. 2, 1999

[54] MYCOBACTERIAL PROTEINS, MICROORGANISMS PRODUCING THEM AND THEIR USE FOR VACCINES AND FOR THE DETECTION OF TUBERCULOSIS

[75] Inventors: Anne Laqueyrerie, Paris; Gilles Marchal, Ivry Sur Seine; Pascale Pescher, Paris; Felix Romain, Fontenay les Briis, all of France

[73] Assignee: Institut Pasteur, Paris Cedex, France

[21] Appl. No.: 641,356

[22] Filed: Apr. 30, 1996

Related U.S. Application Data

[62] Division of Ser. No. 382,184, Feb. 1, 1995, Pat. No. 5,714,593.

[51] Int. Cl.[6] .......................... A61K 39/00; A61K 39/02
[52] U.S. Cl. ..................... 424/185.1; 424/190.1; 424/200.1; 424/203.1; 424/248.1; 435/69.1; 435/69.3; 435/7.32; 530/350; 536/23.1; 536/23.7
[58] Field of Search .................. 435/7.32, 69.1, 435/69.3; 530/350; 424/248.1, 200.1, 190.1, 185.1; 536/23.1, 23.7

[56] References Cited

U.S. PATENT DOCUMENTS 5,599,541  2/1997  Marchal et al. ..................... 424/190.1

FOREIGN PATENT DOCUMENTS 9221758  12/1992  WIPO .

OTHER PUBLICATIONS

Carlin et al. Infect. & Immun. Aug. 1992. 60(8):3136–3142.
Romain et al. Infect & Immun. Feb. 1993. 61(2): 742–750.
Abou–Zeid et al. Infect & Immun. Dec. 1987. 55(12): 3213–3214.
Miura et al. Infect & Immun. Feb. 1983 39( ): 540–545.
Wieles et al. Infect & Immun. Jan. 1994 62 : 552–258.

*Primary Examiner*—James C. Housel
*Assistant Examiner*—Jennifer Shaver
*Attorney, Agent, or Firm*—Oblon, Spivak, McClelland, Maier & Neustadt, P.C.

[57] ABSTRACT

*Mycobacterium tuberculosis* protein having a molecular weight of 20 779 Da, and hybrid proteins containing at least portions of its sequence. These proteins may in particular be used in vaccines or for the detection of specific tuberculosis antibodies.

7 Claims, 18 Drawing Sheets

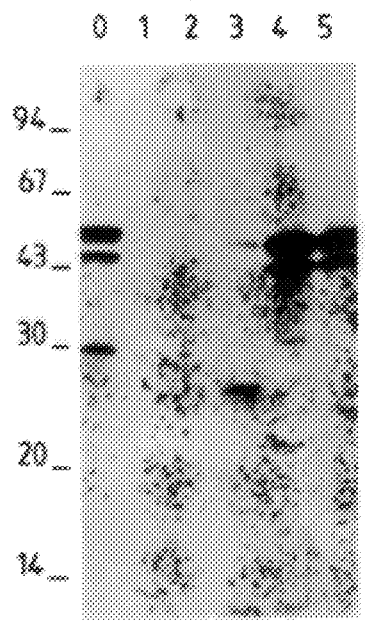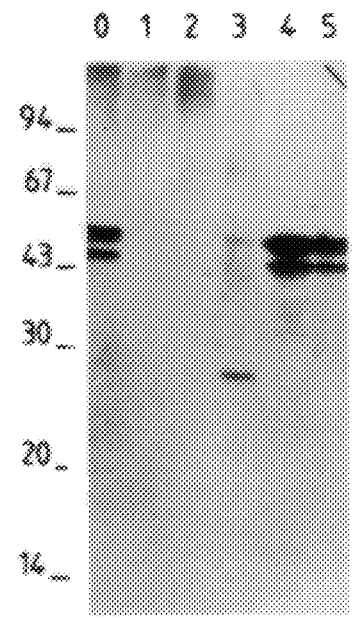
FIG.7A  FIG.7B
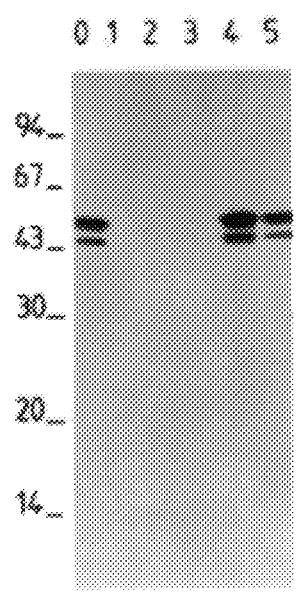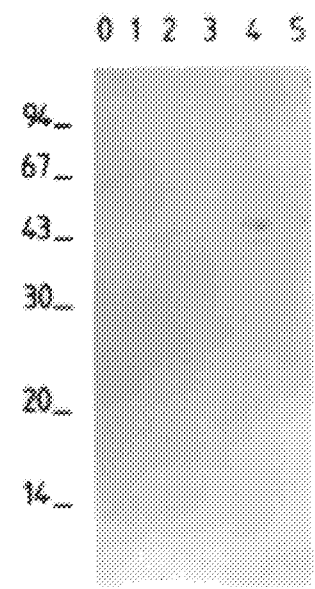
FIG.7C  FIG.7D

● – SUPERNATANT FROM M. BOVIS BCG
△ – SUPERNATANT FROM NON-TRANSFORMED M. SMEGMATIS
□ – SUPERNATANT FROM M. SMEGMATIS TRANSFORMED BY A
    RECOMBINANT CLONE ABLE TO EXPRESS RECOMBINANT PROTEINS
    RECOGNIZED BY THE ANTIBODIES
▽ – SUPERNATANT FROM M. SMEGMATIS TRANSFORMED BY A
    RECOMBINANT CLONE NOT EXPRESSING RECOMBINANT PROTEINS
    RECOGNIZED BY THE ANTIBODIES

FIG.8

```
                                  10        20        30
SEQ. ID 2                    MHQVDPNLTRXKGRLAALAIAAMASASLVTVXVPAT
                             |:||| : |:::||  | ||||::||||  |:: :|:
mln431      XKNPQPQHKQAVLASQXXHGRFVAMNQVDLDSTHRKGLWAILAIAVVASASAFTMPFRAA
                 10        20        30        40        50        60

40        50        60        70        80        90
SEQ. ID 2   ANADPEPAPPVPTTAASPPSTAAAPPAPATPVAPPPPAAANTPNAQPGDPNAAPPPADPN
            |||||:|        |||||:|:|:||  : :| |:|: :::||||||||  |: |||
mln431      ANADPAPL--------PPSTATAAPSPAQEIITPLPGAPVSSEAQPGDPNA--PSLDPN
                              70        80        90       100

100       110       120       130       140       150
SEQ ID. 2   APPPPVIAPNAPQPVRIDNPVGGFSFALPAGWVESDAAHFDYGSALLSKTTGDPPFPGQP
            || | :::|||    ||:|:|||||||:|||||||:|:|:||||:||||:::||  |||
mln431      APYPLAVDPNA---GRITNAVGGFSFVLPAGWVESEASHLDYGSVLLSKAIEQPPVLGQP
               110       120       130       140       150       160

160       170       180       190       200       210
SEQ ID. 2   PPVANDTRIVLGRLDQKLYASAEATDSKAAARLGSDMGEFYMPYPGTRINQETVSLDANG
            : ||:||||||||||||||||||||::  |||:|||||||||:||||||||||::|:|||
mln431      TVVATDTRIVLGRLDQKLYASAEADNIKAAVRLGSDMGEFYLPYPGTRINQETIPLHANG
                170       180       190       200       210       220

220       230       240       250       260       270
SEQ ID. 2   VSGSASYYEVKFSDPSKPNGQIWTGVIGSPAANAPDAGPPQRWFVVWLGTANNPVDKGAA
            ::||||||||||||||:|| ||| |:|:||||::||:||:||||||||||:||||||||
mln431      IAGSASYYEVKFSDPNKPIGQICTSVVGSPAASTPDVGPSQRWFVVWLGTSNNPVDKGAA
                230       240       250       260       270       280

280       290       300       310       320
SEQ ID. 2   KALAESIRPLVAPPPAPAPAPAEPAPAPAPAGEVAPTPTTPTPQRTLPAX
            |:|||||||: :|| ||||:::|||  ::|
mln431      KELAESIRSEMAPIPASVSAPAPVGXAIRHPLRCHCGPCFLDPPPAEQTTVDNRHSSVYT
                290       300       310       320       330       340

FIG. 17
```

MYCOBACTERIAL PROTEINS, MICROORGANISMS PRODUCING THEM AND THEIR USE FOR VACCINES AND FOR THE DETECTION OF TUBERCULOSIS

This is a Division, of application Ser. No. 08/382,184, filed on Feb. 1, 1995, now U.S. Pat. No. 5,714,593.

The object of the present invention is mycobacterial proteins and microorganisms producing them.

It also relates to the use of these proteins in vaccines or for the detection of tuberculosis.

Tuberculosis continues to be a public health problem throughout the world. The annual number of deaths directly related to tuberculosis is about 3 million and the number of new cases of tuberculosis is about 15 million. This number of deaths due to tuberculosis is high even for the developed countries; for example in France it is of the order of 1500 per year, a figure which is certainly underestimated by a factor of 2 or 3 if Roujeau's assessments of the differences between official figures and the results of systematic autopsies are taken into account. The recent increase in tuberculosis cases, or at least the leveling-off of the decrease in the frequency of this disease, must be considered in correlation with the development of the HIV/AIDS epidemic. In total, tuberculosis remains the leading infectious disease in terms of frequency in France and the developed countries, but above all in the developing countries for which it constitutes the principal source of human loss related to a single disease.

At present, a definite diagnosis made by the demonstration of cultivatable bacilli in a sample taken from the patient is only obtained in less than half the cases of tuberculosis. Even for pulmonary tuberculosis, which represents 80 to 90% of the tuberculosis cases, and which is the form of the disease for which the detection of the bacilli is the easiest, the examination of expectorations is only positive for less than half the cases.

The development of more sensitive techniques such as PCR (amplification by polymerase chain reaction), always comes up against the necessity for obtaining a sample. Women and children do not normally spit, and samples for infants frequently require relatively specialized medical intervention (for example ganglionic biopsy or sampling by lumbar puncture of the cephalo-rachidian fluid).

In other respects, inhibitions of the PCR reaction itself exist, of a type such that a sample may be unusable by this technique because of the impossibility of controlling its origins.

Finally, because of its limits of sensitivity (at the best of the order of $10^4$ to $10^5$ bacilli in the sample) the classic bacteriological diagnosis, microscopic examination and culture, requires that there has already been a relatively substantial development of bacilli and thus of the disease.

The detection of specific antibodies directed against *Mycobacterium tuberculosis* should thus be of assistance in the diagnosis of the common forms of the disease for which the detection of the bacilli themselves is difficult or impossible.

Successive generations of research workers have attempted to perfect a serological diagnostic technique for tuberculosis.

For a general review of studies carried out in this area, the application PCT WO-92/21758 may advantageously be referred to.

The techniques reported in the prior art are thus largely based on the preliminary isolation of proteins through their biochemical properties. It is not until after this isolation that the authors have tested the capacity of these proteins to detect those individuals affected by tuberculosis.

Application PCT WO-92/21758 describes a method for unambiguously selecting representative antigens of tubercular infection using serums originating from patients affected by tuberculosis or guinea-pigs immunized by live bacilli. This method, which is distinguished from the majority of the experiments described in the prior art, has led to the isolation of *M. bovis* proteins with molecular weights between 44.5 and 47.5 kD.

The seventeen amino acids of the N-terminal of one of these proteins were determined and are the following:

ALA—PRO—GLU—PRO—ALA—PRO—PRO—VAL—PRO—
 1      2      3      4      5      6      7      8      9
PRO—ALA—ALA—ALA—ALA—PRO—PRO—ALA
 10     11     12     13     14     15     16     17

The article by ROMAIN et al. (1993, Infection and immunity, 61, 742–750) recapitulates the substance of the results described in this international application. It more particularly describes a competitive ELISA assay using a rabbit polyclonal immune serum obtained by immunizing rabbits against the 45–47 kD protein complex described above.

In parallel, a gene library from *Mycobacterium tuberculosis* has been created by JACOBS et al. (1991, Methods Enzymol., 204, 537–557).

This library contains a large number of different clones.

A protein from another Mycobacteria species, *M. leprae*, has moreover been identified by WIELES et al. (1994, Infection and Immunity, 62, 252–258). This protein, named 43 L, has a molecular weight deduced from the nucleotide sequence of about 25.5 Da. Its N terminal has 47% homology with that of the 45–47 kDa protein complex identified in *Mycobacterium bovis* BCG, and whose 17 amino acid sequence is given above.

As stated above, there is a major interest in human medicine, as much from the therapeutic as the diagnostic point of view, in accurately identifying the proteins produced by the Mycobacteria and in particular by *M. tuberculosis*.

The problem which is in fact posed and is as yet unresolved lies in obtaining vaccines against a large number of diseases.

Another problem lies in the detection of diseases induced by the Mycobacteria, such as tuberculosis.

The applicant has thus pursued the determination of the sequence of a *Mycobacterium tuberculosis* protein, which is suspected of playing a major role in the immune response.

The applicant has demonstrated that the group of proteins corresponding to the 45–47 kD complex described above is coded by one and the same gene, and that the calculated molecular mass is different from the molecular mass estimated on polyacrylamide gel, because of its richness in proline.

The object of the present invention is thus a protein having at least a portion of one of the following sequences SEQ ID NO: 2 or SEQ ID NO: 3:

SEQ ID N° 2:

Met His Gln Val Asp Pro Asn Leu Thr Arg Arg Lys Gly Arg Leu

Ala Ala Leu Ala Ile Ala Ala Met Ala Ser Ala Ser Leu Val Thr

Val Ala Val Pro Ala Thr Ala Asn Ala Asp Pro Glu Pro Ala Pro

-continued

Pro Val Pro Thr Thr Ala Ala Ser Pro Ser Thr Ala Ala Ala

Pro Pro Ala Pro Ala Thr Pro Val Ala Pro Pro Pro Ala Ala

Ala Asn Thr Pro Asn Ala Gln Pro Gly Asp Pro Asn Ala Ala Pro

Pro Pro Ala Asp Pro Asn Ala Pro Pro Pro Val Ile Ala Pro

Asn Ala Pro Gln Pro Val Arg Ile Asp Asn Pro Val Gly Gly Phe

Ser Phe Ala Leu Pro Ala Gly Trp Val Glu Ser Asp Ala Ala His

Phe Asp Tyr Gly Ser Ala Leu Leu Ser Lys Thr Thr Gly Asp Pro

Pro Phe Pro Gly Gln Pro Pro Pro Val Ala Asn Asp Thr Arg Ile

Val Leu Gly Arg Leu Asp Gln Lys Leu Tyr Ala Ser Ala Glu Ala

Thr Asp Ser Lys Ala Ala Ala Arg Leu Gly Ser Asp Met Gly Glu

Phe Tyr Met Pro Tyr Pro Gly Thr Arg Ile Asn Gln Glu Thr Val

Ser Leu Asp Ala Asn Gly Val Ser Gly Ser Ala Ser Tyr Tyr Glu

Val Lys Phe Ser Asp Pro Ser Lys Pro Asn Gly Gln Ile Trp Thr
Gly Val Ile Gly Ser Pro Ala Ala Asn Ala Pro Asp Ala Gly Pro
Pro Gln Arg Trp Phe Val Val Trp Leu Gly Thr Ala Asn Asn Pro
Val Asp Lys Gly Ala Ala Lys Ala Leu Ala Glu Ser Ile Arg Pro
Leu Val Ala Pro Pro Pro Ala Pro Ala Pro Ala Pro Ala Glu Pro
Ala Pro Ala Pro Ala Pro Ala Gly Glu Val Ala Pro Thr Pro Thr
Thr Pro Thr Pro Gln Arg Thr Leu Pro Ala

SEQ ID N° 3 :

Asp Pro Glu Pro Ala Pro Pro Val Pro Thr Thr Ala Ala Ser Pro
Pro Ser Thr Ala Ala Ala Pro Pro Ala Pro Ala Thr Pro Val Ala
Pro Pro Pro Pro Ala Ala Ala Asn Thr Pro Asn Ala Gln Pro Gly
Asp Pro Asn Ala Ala Pro Pro Pro Ala Asp Pro Asn Ala Pro Pro
Pro Pro Val Ile Ala Pro Asn Ala Pro Gln Pro Val Arg Ile Asp
Asn Pro Val Gly Gly Phe Ser Phe Ala Leu Pro Ala Gly Trp Val
Glu Ser Asp Ala Ala His Phe Asp Tyr Gly Ser Ala Leu Leu Ser
Lys Thr Thr Gly Asp Pro Pro Phe Pro Gly Gln Pro Pro Pro Val
Ala Asn Asp Thr Arg Ile Val Leu Gly Arg Leu Asp Gln Lys Leu

-continued

Tyr Ala Ser Ala Glu Ala Thr Asp Ser Lys Ala Ala Ala Arg Leu
Gly Ser Asp Met Gly Glu Phe Tyr Met Pro Tyr Pro Gly Thr Arg
Ile Asn Gln Glu Thr Val Ser Leu Asp Ala Asn Gly Val Ser Gly
Ser Ala Ser Tyr Tyr Glu Val Lys Phe Ser Asp Pro Ser Lys Pro
Asn Gly Gln Ile Trp Thr Gly Val Ile Gly Ser Pro Ala Ala Asn
Ala Pro Asp Ala Gly Pro Pro Gln Arg Trp Phe Val Val Trp Leu
Gly Thr Ala Asn Asn Pro Val Asp Lys Gly Ala Ala Lys Ala Leu
Ala Glu Ser Ile Arg Pro Leu Val Ala Pro Pro Pro Ala Pro Ala
Pro Ala Pro Ala Glu Pro Ala Pro Ala Pro Ala Pro Ala Gly Glu
Val Ala Pro Thr Pro Thr Thr Pro Thr Pro Gln Arg Thr Leu Pro
Ala

The invention also relates to hybrid proteins having at least a portion of the sequences SEQ ID NO. 2 or SEQ ID NO. 3 and a sequence of a peptide or a protein able to induce an immune response in man or in animals.

Advantageously, the antigenic determinant is such that it is able to induce a humoral and/or cellular response.

Such a determinant may be of a diverse nature and notably an antigenic protein fragment, advantageously a glycoprotein, utilized in order to obtain immunogenic compositions able to induce the synthesis of antibodies directed against multiple epitopes.

These hybrid molecules may also be constituted in part by a molecule carrying the sequences SEQ ID NO: 2 or SEQ ID NO: 3 combined with a portion, in particular an epitope, of diphtheria toxin, tetanus toxin, the HBS antigen of the HBV virus, the VPl antigen of the poliomyelitis virus or any other viral toxin or antigen.

The processes for synthesizing the hybrid molecules include the methods used in genetic engineering for producing hybrid DNA coding for the required protein or peptide sequences.

The present invention also includes proteins having secondary differences or limited variations in their amino acid sequences which do not functionally modify them by comparison with the proteins having the sequences SEQ ID No: 2 and SEQ ID No: 3, or with hybrid proteins containing at least a portion of these sequences.

It should be noted that the present invention has revealed a very large difference in molecular weight between the weights calculated for the protein corresponding to the sequence SEQ ID No: 3, which is of 28779 Da, and that of the complex, evaluated by SDS gel, which is of the order of 45–47 kD. This difference is probably due to the high frequency (21.7%) of proline in the polypeptide chain.

Other objects of the invention are oligonucleotides, RNA or DNA, coding for the proteins defined above. One such nucleotide has advantageously at least a portion of the following sequence SEQ ID NO: 1:

```
GT GCTCGGGCCC AACGGTGCGG GCAAGTCCAC CGCCCTGCAT GTTATCGCGG

GGCTGCTTCG CCCCCGACGC GGGCTTGGTA CGTTTGGGGG ACCGGGTGTT

GACCGACACC GAGGCCGGGG TGAATGTGGC GACCCACGAC CGTCGAGTCG

GGCTGCTGTT GCAAGACCCG TTGTTGTTTC CACACCTGAG CGTGGCCAAA

AACGTGGCCT TCGGACCACA ATGCCGTCGC GGGATGTTTG GGTCCGGGCG

CGCGCTAGGA CAAGGGCGTC GGCACTGCGA TGGCTGCGCG AGGTGAACGC

CGAGCAGTTC GCCGACCGTA AGCCTCGTCA GCTATCCGGG GGCCAAGCCC

AGCGCGTCGC CATCGCGCGA GCGTTGGCGG CCGAACCGGA TGTGTTGCTG

CTCGACGAGC CGCTGACCGG ACTCGATGTG GCCGCGGCCG CGGGTATCCG

TTCGGTGTTG CGTAGTGTCG TCGCGAGGAG CGGTTGCGCG GTAGTCCTGA

CGACCCATGA CCTGCTGGAC GTGTTCACGC TGGCCGACCG GGTATTGGTG

CTCGAGTCCG GCACGATCGC CGAGATCGGC CCGGTTGCCG ATGTGCTTAC

CGCACCTCGC AGTCGTTTCG GAGCCCGTAT CGCCGGAGTC AACCTGGTCA

ATGGGACCAT TGGTCCGGAC GGCTCGCTGC GCACCCAGTC CGGCGCCCAC

TGGTACGGCA CCCCGGTCCA GGATTTGCCT ACTGGGCATG AGGCAATCGC

GGTGTTCCCG CCGACGGCGG TGGCGGTGTA TCCGGAACCG CCGCACGGAA

GCCCGCGCAA TATCGTCGGG CTGACGGTGG CGGAGGTGGA TACCCGCGGA

CCCACGGTCC TGGTGCGCGG GCATGATCAG CCTGGTGGCG CGCCTGGCCT

TGCCGCATGC ATCACCGTCG ATGCCGCCAC CGAACTGCGT GTGGCGCCCG

GATCGCGCGT GTGGTTCAGC GTCAAGGCGC AGGAAGTGGC CCTGCACCCG

GCACCCCACC AACACGCCAG TTCATGAGCC GACCCGCGCC GTCCTTGCGT

CGCGCCGTTA ACACGGTAGG TTCTTCGCCA TGCATCAGGT GGACCCCAAC

TTGACACGTC GCAAGGGACG ATTGGCGGCA CTGGCTATCG CGGCGATGGC

CAGCGCCAGC CTGGTGACCG TTGCGGTGCC CGCGACCGCC AACGCCGATC

CGGAGCCAGC GCCCCCGGTA CCCACAACGG CCGCCTCGCC GCCGTCGACC

GCTGCAGCGC CACCCGCACC GGCGACACCT GTTGCCCCCC CACCACCGGC

CGCCGCCAAC ACGCCGAATG CCCAGCCGGG CGATCCCAAC GCAGCACCTC

CGCCGGCCGA CCCGAACGCA CCGCCGCCAC CTGTCATTGC CCCAAACGCA
```

-continued

```
CCCCAACCTG  TCCGGATCGA  CAACCCGGTT  GGAGGATTCA  GCTTCGCGCT

GCCTGCTGGC  TGGGTGGAGT  CTGACGCCGC  CCACTTCGAC  TACGGTTCAG

CACTCCTCAG  CAAAACCACC  GGGGACCCGC  CATTTCCGG   ACAGCCGCCG

CCGGTGGCCA  ATGACACCCG  TATCGTGCTC  GGCCGGCTAG  ACCAAAAGCT

TTACGCCAGC  GCCGAAGCCA  CCGACTCCAA  GGCCGCGGCC  CGGTTGGGCT

CGGACATGGG  TGAGTTCTAT  ATGCCCTACC  CGGGCACCCG  GATCAACCAG

GAAACCGTCT  CGCTCGACGC  CAACGGGGTG  TCTGGAAGCG  CGTCGTATTA

CGAAGTCAAG  TTCAGCGATC  CGAGTAAGCC  GAACGGCCAG  ATCTGGACGG

GCGTAATCGG  CTCGCCCGCG  GCGAACGCAC  CGGACGCCGG  GCCCCCTCAG

CGCTGGTTTG  TGGTATGGCT  CGGGACCGCC  AACAACCCGG  TGGACAAGGG

CGCGGCCAAG  GCGCTGGCCG  AATCGATCCG  GCCTTTGGTC  GCCCCGCCGC

CGGCGCCGGC  ACCGGCTCCT  GCAGAGCCCG  CTCCGGCGCC  GGCGCCGGCC

GGGGAAGTCG  CTCCTACCCC  GACGACACCG  ACACCGCAGC  GGACCTTACC

GGCCTGACC
```

The present invention also relates to a microorganism producing one of the proteins such as are described above and in particular a microorganism secreting such an protein.

The microorganism is preferentially a bacterium such as *Mycobacterium bovis* BCG. These bacteria are already used in man in order to obtain an immunity against tuberculosis.

The production of hybrid proteins according to the present invention in *M. bovis* BCG has specific advantages. *M. bovis* BCG is a strain widely used for vaccination purposes and which is accepted as being innocuous to man. After injection into the human body it develops slowly over 15 days to 1 month, which leads to excellent presentation of the antigen against which a response is desired from the organism.

On the other hand *Mycobacterium leprae*, which is the agent of leprosy in man, is little known. This bacterium has not up till now been able to be cultivated on a culture medium and has a very long growth period by comparison with *M. bovis*.

Its potential pathogenicity is moreover an obvious argument for not using it for vaccination purposes.

Proteins with the sequences SEQ ID NO: 2 or SEQ ID NO: 3 have the advantage of being recognized by the antibody present in tuberculosis patients and thus constitute a priori highly immunogenic antigens.

The proteins originate from *M. tuberculosis*, which is a species very close to *M. bovis*, these two bacteria being responsible for tuberculosis in man and cattle respectively.

The proteins originating from *M. tuberculosis* are thus able to be expressed in *M. bovis* and to be excreted in the culture medium by cells possessing a signal peptide.

Since *M. bovis* has the advantages listed above for vaccination in man and since in addition the proteins corresponding to the SEQ ID NO: 2 and SEQ ID NO: 3 sequences induce a strong immune response in man, it is especially advantageous to produce hybrid proteins in *M. bovis* which carry a portion of the proteins originating from *M. tuberculosis*.

It is well known that the pathogenic microbial antigens against which a vaccination is being sought can only induce a very weak response in man unless they are presented in a specific manner.

The present invention resolves this problem in two ways:
  on the one hand by presenting the hybrid protein on the surface of *M. bovis* BCG, and/or excreted by the bacteria
  and on the other by combining an antigenic determinant known to induce a strong immune response, i.e. the antigenic determinant of one of the proteins with SEQ ID NO: 2 or SEQ ID NO: 3, with an antigenic determinant inducing a weak response when it is injected alone.

The combination of the antigenic determinant of one of the proteins SEQ ID NO: 2 or SEQ ID NO: 3 allows an amplification of the immune response against the second antigenic determinant of the hybrid protein. This phenomenon can perhaps be compared to the hapten carrier effect.

It is clear that such an operation cannot be envisaged with a protein originating from *M. leprae*, such as that described in the article by Wieles et al. (1994, cited above), since on the one hand because of the much larger difference between *M. tuberculosis* and *M. leprae*, such a protein might not be properly expressed, and on another the immune response induced by this *M. leprae* protein is less well known. In addition the introduction of a protein from a pathogenic species for vaccination purposes constitutes a potential risk to human health which the pharmaceutical industry is reluctant to accept.

All these arguments contribute to a distinction between the protein sequences SEQ ID NO: 2 and SEQ ID NO: 3 and the *M. leprae* protein described by Wieles et al. (1994, cited above), despite their apparent sequence homologies (see later in FIG. 17).

The present invention also relates to vaccines or drugs containing at least one protein or microorganism such as those previously defined.

Vaccines containing nongrafted proteins may be used to immunize individuals against tuberculosis. Grafted proteins carrying an epitope originating from a biological agent other than *M. bovis* may be used for immunization against other diseases.

As an indication, 1 to 500 μg of protein per dose for an individual, or $10^3$ to $10^7$ recombinant bacteria per individual, may be used intradermally.

Another object of the present invention is a pharmaceutical composition containing at least a pharmaceutically effective quantity of a protein or a microorganism such as previously described in combination with pharmaceutically compatible diluents or adjuvants.

Another object of the present invention is a process for detecting the specific tuberculosis antibodies, in which a biological fluid, in which the presence of said antibodies is sought, is brought into contact with a protein such as that described above.

Advantageously, said protein is fixed on a support.

Such detection could in particular be implemented by the Western Blot (immuno-imprint) method, by an enzyme immunoassay method (ELISA) or a radioimmunoassay method (RIA), by use of an assay kit, containing the proteins as well as in particular buffer solutions allowing the immunological reaction to be carried out and if necessary substances allowing the antibody-antigen complex formed to be revealed.

The present invention is illustrated without in any way being restricted by the following examples and the annexed drawings in which:

FIG. 1 is an optical density (OD) profile at 240 nm of the molecular filtration (Si 300) of an *M. tuberculosis* fraction not retained on an ion-exchange column under the conditions described later.

FIG. 2 shows the optical density profile at 220 nm of the separation on a high-pressure ion-exchange column (DEAE) of molecules originating from fraction 1 obtained from the previous molecular filtration.

FIG. 3 shows the optical density profile at 220 nm of the reversed phase column chromatography of fraction 1 from the previous ion-exchange chromatography.

FIGS. 4A to 4E are photographs of PVDF membranes revealed by respectively

- a colorant for molecules (4A) transferred on the PVDF membrane. Aurodye coloration (Amersham);
- a mixture of serums from guinea-pigs immunized with live (4B) or dead (4C) bacilli.;
- a serum (4D) from rabbit immunized with purified antigens from BCG (Infection and Immunity (1993) 61 742–750)
- a monoclonal antibody reference I-1081 (4E).

These PVDF membranes had previously received the molecules from fractions separated on the low-pressure ion-exchange column separated by electrophoresis on acrylamide gel. Track 0 corresponds to the raw starting material, track 1 to the non-retained fraction, and track 2 to the fraction retained.

FIG. 5A to 5E represent PVDF membranes corresponding to a gel obtained by the migration of the 5 fractions (1 to 5) obtained on the Si 300 gel filtration column and the non-retained fraction from the low-pressure DEAE column (0). After transfer of identical gels on PVDF membranes one was revealed by use of a protein colorant [Aurodye, Amersham (5A)], or a serum from guinea-pigs immunized with live (5B) or dead (5C) bacilli, or a rabbit serum (5D) or a monoclonal antibody (5E).

FIGS. 6A to 6E show PVDF membranes corresponding to a gel obtained by the migration of fractions obtained on a high-pressure ion-exchange column (1 to 3) and fraction 1 obtained by filtration on a molecular sieve (well 0), said membrane being revealed :

- by a protein colorant (6A),
- by an antibody from the serum of guinea-pigs immunized with respectively live (6B) or dead (6C) bacilli,
- by a rabbit serum (6D),
- by a monoclonal antibody (6E).

FIGS. 7A to 7D show the imprint of gels on membranes corresponding to the migration of the fraction 1 obtained on ion-exchange column (0) and the fractions obtained by reversed phase chromatography (1 to 5), revealed by the same reagents as for FIGS. 6A to 6B, 6D to 6E with the same codes.

FIG. 8 shows the screening of the gene library for the expression of *M. tuberculosis* H37Rv in *M. smegmatis*. The supernatants of *M. bovis* BCG, non-transformed *M. smegmatis* and *M. smegmatis* transformed by the recombinant clones expressing or not expressing the recombinant proteins recognized by the antibodies, were tested at different dilutions.

FIG. 9 shows the migration in agarose gel of three cosmids selected from the library, electropored in *E. coli* and extracted by alkaline lysis.

FIG. 10 represents the migration on gel of the cosmid DNA of pLAl extracted from *E. coli* NM554 digested by BamHI (a), SmaI (b), HpaI (c), NotI (d), SspI (e), EcoRI (f) and Hind III (g).

FIG. 11 illustrates the expression of the 45/47 kDa proteins in mycobacteria. The supernatants from the 7 day bacterial culture were washed and concentrated on an Amicon PM10 membrane, freeze-dried and analyzed as immuno-imprints. The proteins were revealed by polyclonal antibodies from rabbit serum diluted to 1/500.

The wells contained respectively:

(1) 0.25 μg of the purified 45/47 kDa proteins from *M. bovis* BCG, (2) 5 μg of supernatant of *M. smegmatis* $mc^2155$ transformed by pLA1, (3) 5 μg of supernatant from non-transformed *M. smegmatis* $mc^2155$, (4) 5 μg of *M. bovis* BCG supernatant.

FIG. 12 illustrates the expression of the 45/47 kDa proteins in mycobacteria. The supernatants from the bacterial culture were washed and concentrated on an Amicon PM10 membrane, then freeze-dried and analyzed in a competitive ELISA assay. Different concentrations of the freeze-dried supernatants were revealed with a 1/8000th dilution of rabbit polyclonal serum, and this mixture was then transferred into wells in which the purified proteins had been fixed.

FIGS. 13A and 13B are plasmid profiles (13A) and BamH I restriction profiles (13B) of different pUC18:: *M. tuberculosis* H37Rv recombinant clones, obtained by ligation of fragments from a BamH I digestion of the pLA1 cosmid in pUC18. This figure shows 21 of the 36 clones studied. The wells "p" correspond to the reference vector pUC18, and wells "m" to size markers which are fragments of the pKN plasmid cleaved by Pvu II.

FIG. 14 is the restriction map for inserts allowing the expression of the 45/47 kDa proteins in E. coli. A group of clones was obtained by deletions from the PLA34 and pLA4 plasmids, containing the 3 kb insert cloned in both directions. The arrows show the direction of sequence determination from these clones through "direct" and "inverse" primers.

| B, BamH I | S, Sma I | E, EcoR I | K, Kpn I |
| H, Hind III | Sa, Sal I | Sp, Sph I | |

FIG. 15 illustrates the expression of the 45/47 kDa proteins in E. coli. The bacterial culture lysates were analyzed by immuno-imprints.

The proteins were revealed by rabbit polyclonal antibodies purified on DEAF, then absorbed on an E. coli lysate immobilized on a Sepharose-4B column activated by cyanogen bromide.

The wells contained respectively:

(1) 0.2 µg of the purified 45/47 kDa proteins, (2) 25 µg of lysate of E. coli XL-Blue transformed by PLA34-2, (3) 25 µg of lysate of E. coli XL-Blue transformed by pLA34, (4) 25 µg of lysate of non-transformed E. coli XL1-Blue.

FIG. 17 is a comparison of the sequence SEQ ID NO: 2 according to the invention and the sequence of the protein from M. leprae (mln 431).

Figure 1:
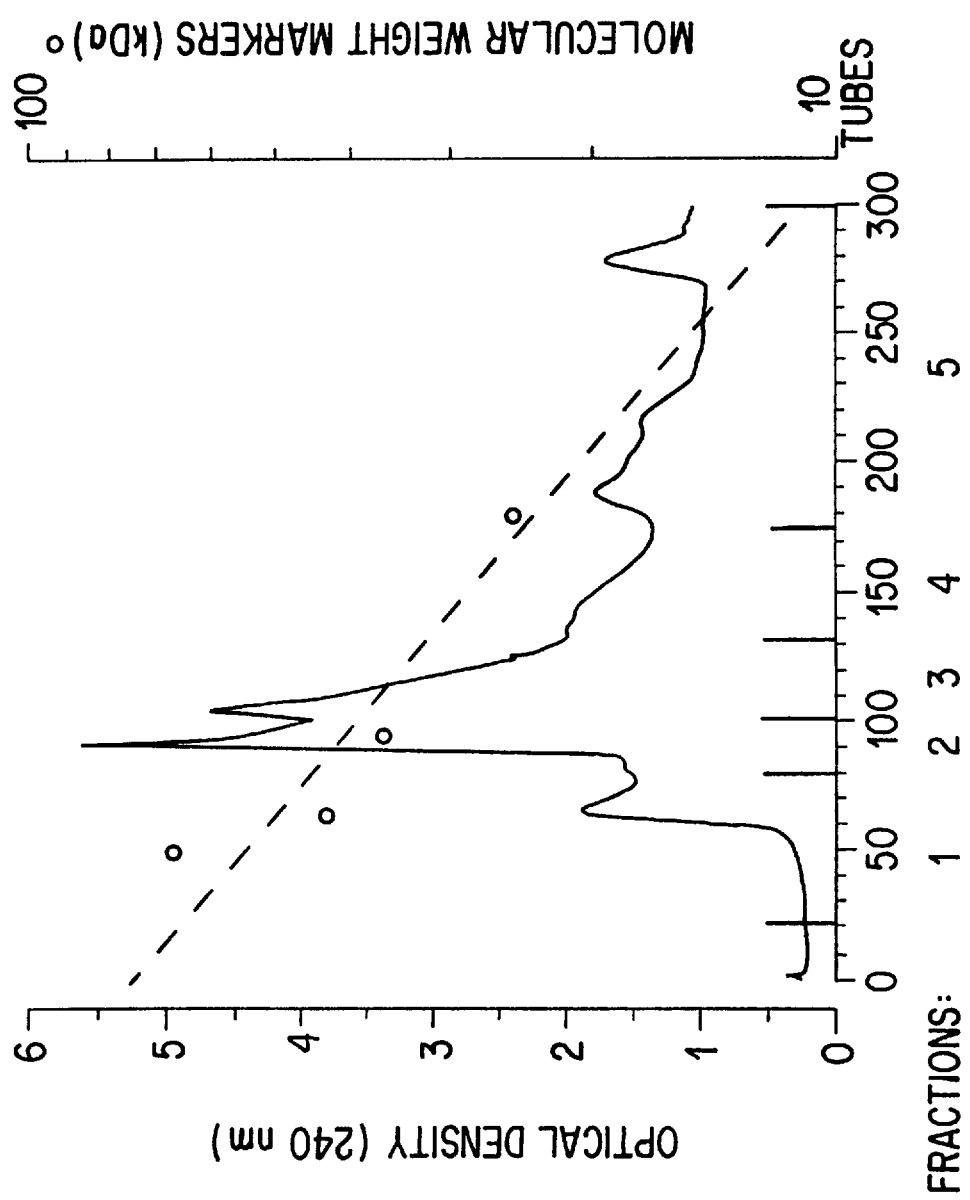

EXAMPLE 1:

Purification process for the M. tuberculosis antigens

1) Obtaining the antigens:

Cultures of M. tuberculosis (strain H37Rv) were made in flasks containing 130 ml of Sauton's synthetic medium according to the conventional technique described for the culture of BCG (Gheorghiu et al., Bull. Institut Pasteur 1983, 81: 281–288). The culture medium was harvested after 20 days at 37° C., decanted and filtered (0.22 µm) at laboratory temperature. These operations were carried out in a glove box for safety reasons. The harvested and filtered culture medium was again filtered on a 0.22 µm filter under a safety hood before being used for the following operations:

After application to an Amicon (PM10) membrane under nitrogen at 2 bar and 4° C., the culture medium was washed intensively with retro-osmosed water containing 4% of butanol, then concentrated 10 to 20 times with respect to the original volume. This concentrated culture medium, containing the molecules not excluded by the Amicon PM10 membrane, was freeze-dried, weighed and stored as a powder at −20° C. The 12 g of starting material used for the purification process described below were obtained from 70 liters of culture medium.

Purification scheme:

2) Low-pressure ion-exchange column:

A low-pressure preparative ion-exchange column of height 300 mm and diameter 32 mm was prepared with approximately 240 ml of Triacyl M gel (SEPRACOR). It was equilibrated with a buffered saline solution (10 mM Na$_2$HPO$_4$/NaH$_2$PO$_4$, pH=7, and 10 mM NaCl) containing 4% of butanol.

The concentrated and freeze-dried material prepared as in the previous stage was dissolved (in the previously described buffered saline solution) then ultracentrifuged—for 120 minutes at 40,000 G. Only the upper portion (4/5) of the centrifuged solution was collected and placed under the control of the peristaltic pump on the ion-exchange column. A first major fraction not retained by the column was collected. A second fraction was obtained after elution of the column by a buffered saline solution (10 mM Na$_2$HPO$_4$/NaH$_2$PO$_4$, pH=7.5 and 1 M NaCl). After application onto an Amicon (PM10) membrane under 2 bar pressure, each fraction was intensively washed with retro-osmosed water containing 4% of butanol, and concentrated approximately 15 times. The fraction not retained on the column contained 2.9 g of material and the majority of the molecules which were then purified in the following stages. The fraction retained on the column and then eluted by the salt solution contained approximately 1.01 g of material.

3) Gel filtration

A high-pressure preparative Si 300 column, 3 µm, of 50×750 mm (SERVA), was equilibrated with a buffered saline solution (50 mM Na$_2$HPO$_4$ adjusted to pH 7.5 with KH$_2$HPO$_4$) containing 4% of butanol; this solution had previously been filtered on a membrane (0.22 µm). The column flow was adjusted to 1.25 ml bar per min: the maximum pressure, set at 45 bar, was not reached.

The material to be injected onto the column was prepared at a concentration of 50 mg/ml in the buffer/butanol solution. 10 ml samples were prepared and frozen at −20° C. Each 10 ml sample, refiltered after thawing and injected onto the column, contained approximately 500 mg of crude material. The optical density profiles at 240 nm are shown in FIG. 1 for a typical separation sequence. The five principal fractions selected based on the profile were concentrated at 4° C. and intensively washed on an Amicon PM10 membrane with retro-osmosed water containing 4% of butanol. Each concentrated fraction was freeze-dried, weighed and then stored at −20 C. Fraction 1 from this stage contained the principal molecules recognized by the antibodies from guinea-pigs immunized with live bacilli or by the antibodies from tuberculosis patients. Only this fraction was used for the following stage.

4) Ion-exchange column:

A DEAE-TSK 5PW preparative column 21.5×150 mm (LKB) was equilibrated with a buffered saline solution (10 mM Na$_2$HPO$_4$/NaH$_2$PO$_4$, pH=7.5 and 10 mM NaCl) containing 4% of butanol. The maximum pressure was below 30 bar for a 6 ml/min flow. Only the NaCl concentration was changed (1 M) for the elution buffer. A linear gradient was applied according to the scheme shown in FIG. 2 after injection of a 4 ml sample volume containing in total 100 mg of the above material. The principal fractions were collected according to the optical density profile at 240 nm. These fractions were concentrated and washed on an Amicon PM10 membrane with retro-osmosed water containing 4% of butanol, then freeze-dried. After weighing, each fraction was stored at −20° C. Only fraction 1 from this stage contained the majority of the molecules recognized by the antibodies from guinea-pigs immunized with live bacteria; these were used for the following separation stage.

Figure 3:
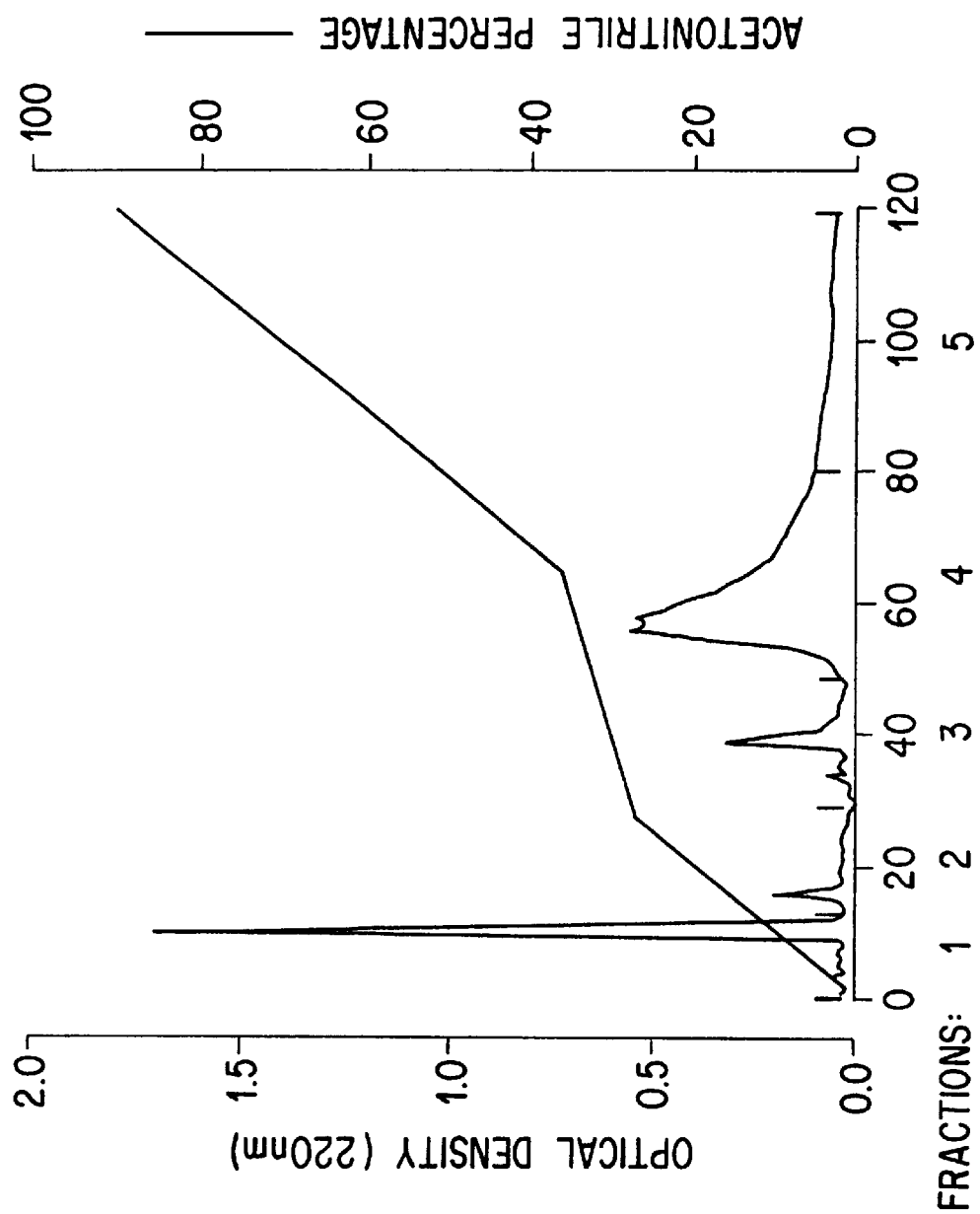
Figure 4A:
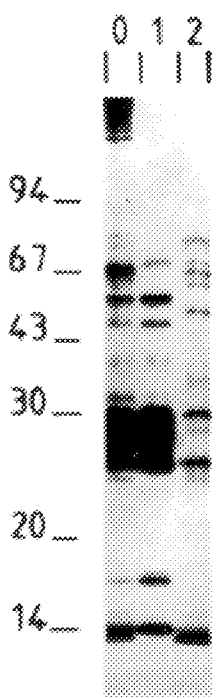
Figure 4B:
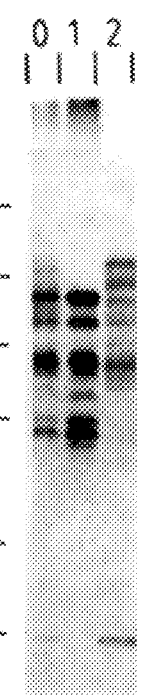
Figure 4C:
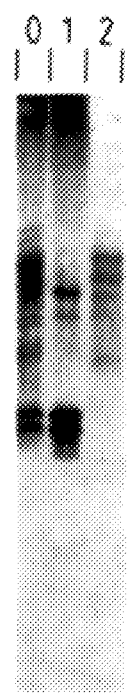
Figure 4D:
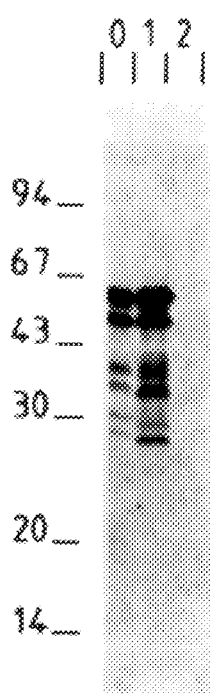
Figure 4E:
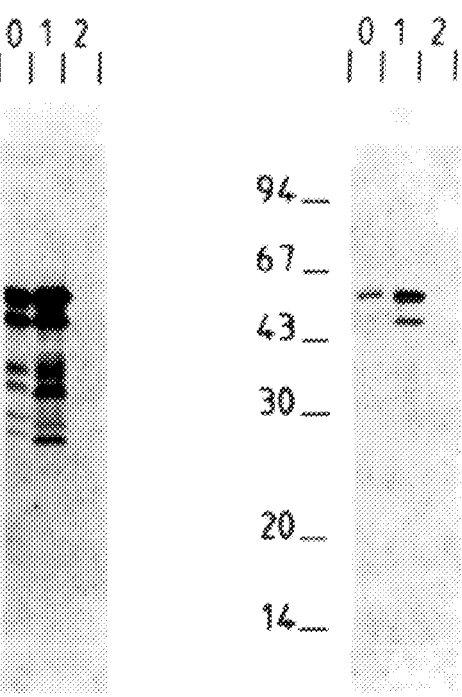

5) Reversed phase column:

A 4.6×250 mm RP 300 C$_a$ 10 µm (Aquapore Brownlee lab.) column was equilibrated with an ammonium acetate buffer (20 mM NH$_4$COOCH$_3$) filtered at 0.22 µm with a flow of 2 ml/min under a maximum pressure of 115 bar. The elution buffer containing 90% of acetonitrile was applied according to the profile shown in FIG. 3 after injection of a 10 mg sample in a 1 ml volume. The optical density profile at 220 nm enabled the separation of five major fractions which were concentrated by vacuum evaporation at 40° C., then freeze-dried.

6) Immunodetection of the antigens:

10% polyacrylamide 0.1% SDS denaturing gels were prepared according to the conventional technique of Laemmli (Nature, 1970, 277: 680–685). Samples containing between 10 and 2 µg of material, according to the purification stage, were applied in a buffer containing 5% of mercaptoethanol, 3% of SDS and a trace of bromophenol blue in a 10 µl volume in each track of the gel. After electrophoresis to the limit of migration of the blue, the molecules present in the samples were transferred on a sheet of PVDF (Millipore) by the application of a moderate electric field overnight [Harlow and Lane, Antibodies, A Laboratory Manual, Cold Spring Harbor Laboratory (Publishers), 1988].

A coloration of the PVDF sheet by a solution of Coomasie blue for less than a minute, followed by a decoloration, permitted identification of the molecular weight markers, whose shape was outlined with a pencil mark. After total decoloration, the sheet was washed for 30 min at laboratory temperature with PBS+Triton X100 3%, then 3 times for 5 min with PBS alone. The sheet was then saturated with PBS containing 5% of powdered skimmed milk for 1 h at 37° C., then washed three times with PBS +Tween 20 (0.2%).

An incubation was carried out with the antiserums diluted to 1/20th in the PBS+Tween 20 buffer (0.2%)+powdered milk (5%) for 1 h 30 at 37° C. with periodic agitation. Three further washings with PBS+Tween were then carried out before incubation with the anti-immunoglobulin antibodies marked with alkaline phosphatase. The human and guinea-pig anti-immunoglobulin antibodies, marked with phosphatase (Biosys), were used at a final dilution of 1/2500 in PBS+Tween 20 (0.2%)+milk (5%). After incubation for 1 h 30 min at 37° C., the PVDF sheets were washed three times with PBS+Tween, then incubated at laboratory temperature for 5 to 10 min in the revealing buffer containing BCIP and NBT (Harlow and Lane, cited above). The reaction was stopped and after drying the sheets themselves were photographed.

7) Amino acid composition:

An analysis of the total amino acid composition was carried out for each chromatographic fraction in the Institut Pasteur Organic Chemistry Department. A Beckmann LS 6300 analyzer was used.

The total composition expressed as amino acid frequency of the 45–47 kD proteins was as follows: ASN/ASP: 10.4%; THR: 5.7%; SER: 5.6%; GLN/GLU: 6.3%; GLY: 7.1%; ALA: 19.3%; VAL: 6.2%; ILE: 2.2%; LEU: 4.4%; TYR: 2.2%; PHE: 2.4%; LYS: 2.7%; ARG: 2.7%; PRO 20.9%.

EXAMPLE 2:

Determination of the immunological specificity of the proteins and protein fractions of M. tuberculosis and isolation of the antigens recognized by the antibodies from guinea-pigs immunized with live bacilli.

Groups of 12 to 15 guinea-pigs (Hartley females of 250 to 300 g at the beginning of the experiment) received either live mycobacteria ($2 \times 10^7$ viable units of BCG in two intradermic injections in 0.1 ml of saline solution), or 2 mg of heat-killed (120° C., 30 min) mycobacteria from the same strain intramuscularly in 0.5 ml of a saline solution emulsion in incomplete Freund's adjuvant (1/1). Serum samples from different groups of guinea-pigs were taken 7 to 12 months after immunization, filtered (0.22 µm), then separated into small volumes which were frozen and stored at −20° C. Tests of several groups of antiserums were carried out (5 after immunization with live bacteria and 6 after immunization with killed bacteria). The results reported were obtained with a group of serums representative of each type of immunization; the differences between groups were minimal for the same immunization method.

1) Separation stage on a low-pressure ion exchange column.

The culture medium (washed and concentrated on an Amicon PM10 membrane then freeze-dried) was ultracentrifuged then loaded onto a low-pressure ion-exchange column. Two fractions were obtained, one not retained by the column and the other eluted by a high-molarity buffered solution, and were washed and concentrated on an Amicon PM10 membrane, then freeze-dried.

Each fraction (10 µg) was placed on an SDS gel track and then, after the electrophoresis sequence, transfer on a PVDF membrane and immunodetection, the fractions containing the predominant molecules reacting with the different serums were identified.

FIG. 4 shows the immuno-imprints of identical gels revealed with a colorant for the transferred proteins (Aurodye-Amersham) (4A) or serums from guinea-pigs immunized with live (4B) or dead (4C) bacilli. The immuno-imprints 4D and 4F were revealed respectively with a rabbit serum directed against molecules identical to BCG (Infection and Immunity, 1993, 61, 742–750) and the supernatant of the I-1081 hybridoma producing of a monoclonal antibody, deposited with the Collection Nationale de Cultures de Microorganismes (CNCM) at the Institut Pasteur. Only the fraction not retained on the column contained the 45/47 kDa molecules recognized by the serums from guinea-pigs immunized with the live or dead bacilli or recognized by the supernatant of the hybridoma described above.

2) Molecular filtration stage on Si 300.

The non-retained fraction from the previous stage was injected in a sample volume of 10 ml containing 500 mg of material onto the Si 300 column. Fractions 1 to 5 were separated according to the profile shown in FIG. 1, the products from successive injections were combined together, then washed, concentrated and freeze-dried.

Each fraction (10 µg) was placed on an SDS gel track; then, after the electrophoresis sequence, transfer on PVDF membrane and immunodetection, the fractions containing the predominant of the proteins reacting with the different serums were identified.

Figures 5A, 5B, 5C:
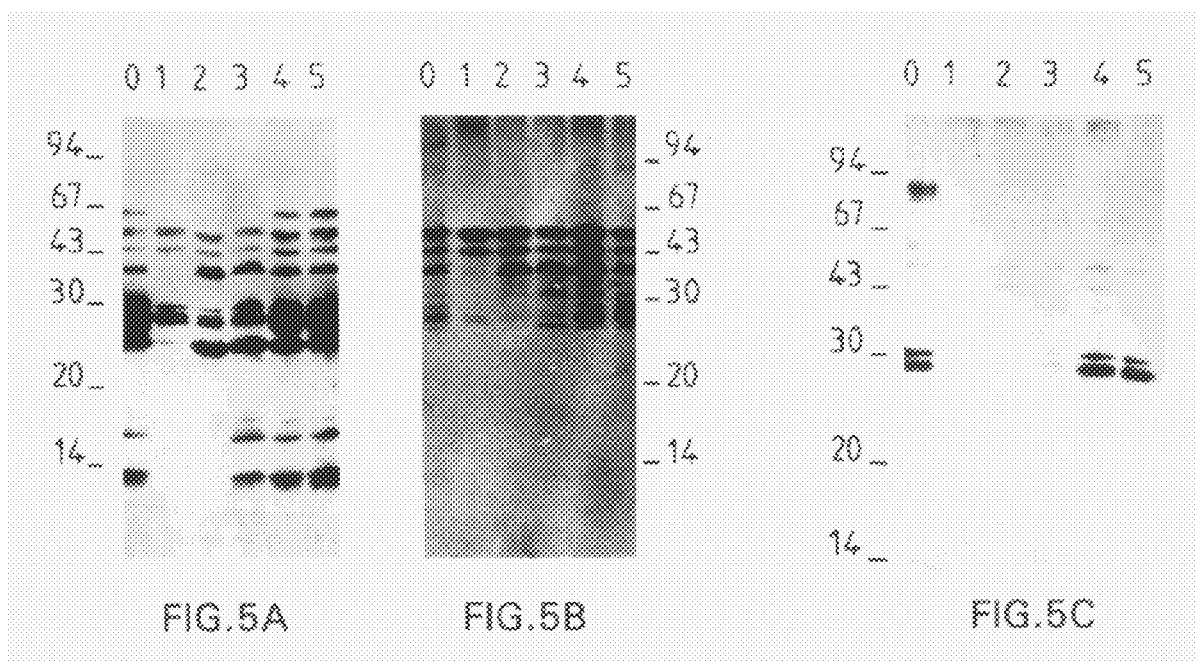
Figure 5D:
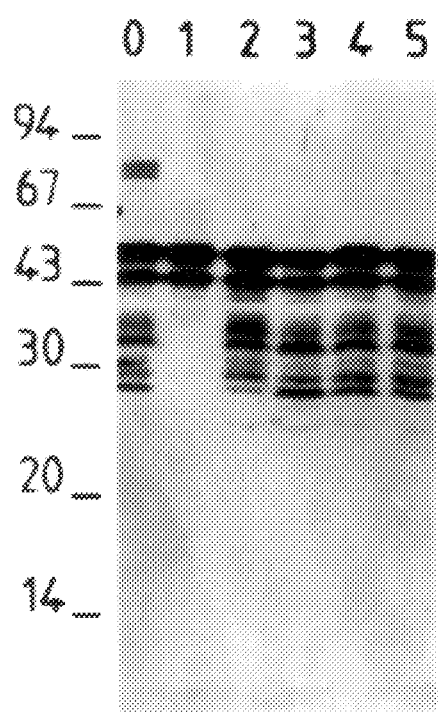
Figure 5E:
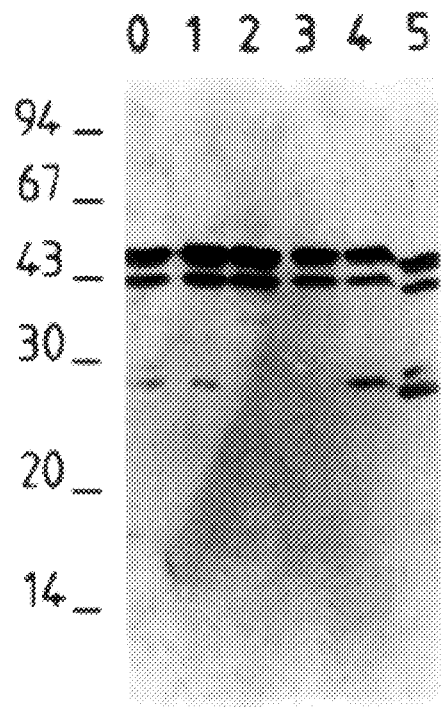

FIG. 5 shows the immuno-imprints of identical gels revealed after protein coloration (Aurodye-Amersham) or with the serums from guinea-pigs immunized with live (5B) or dead (5C) bacilli. The immuno-imprints 5D and 5E were revealed with respectively a rabbit serum directed against these molecules purified from BCG and with the I-1081 monoclonal antibody.

Two 45 and 47 kD antigens present in fraction 1 were mainly recognized by the antibodies from animals immunized with live bacilli or with the polyclonal rabbit serum or with the monoclonal antibody. This fraction was selected for the second purification stage.

3) Ion exchange stage.

Figure 2:
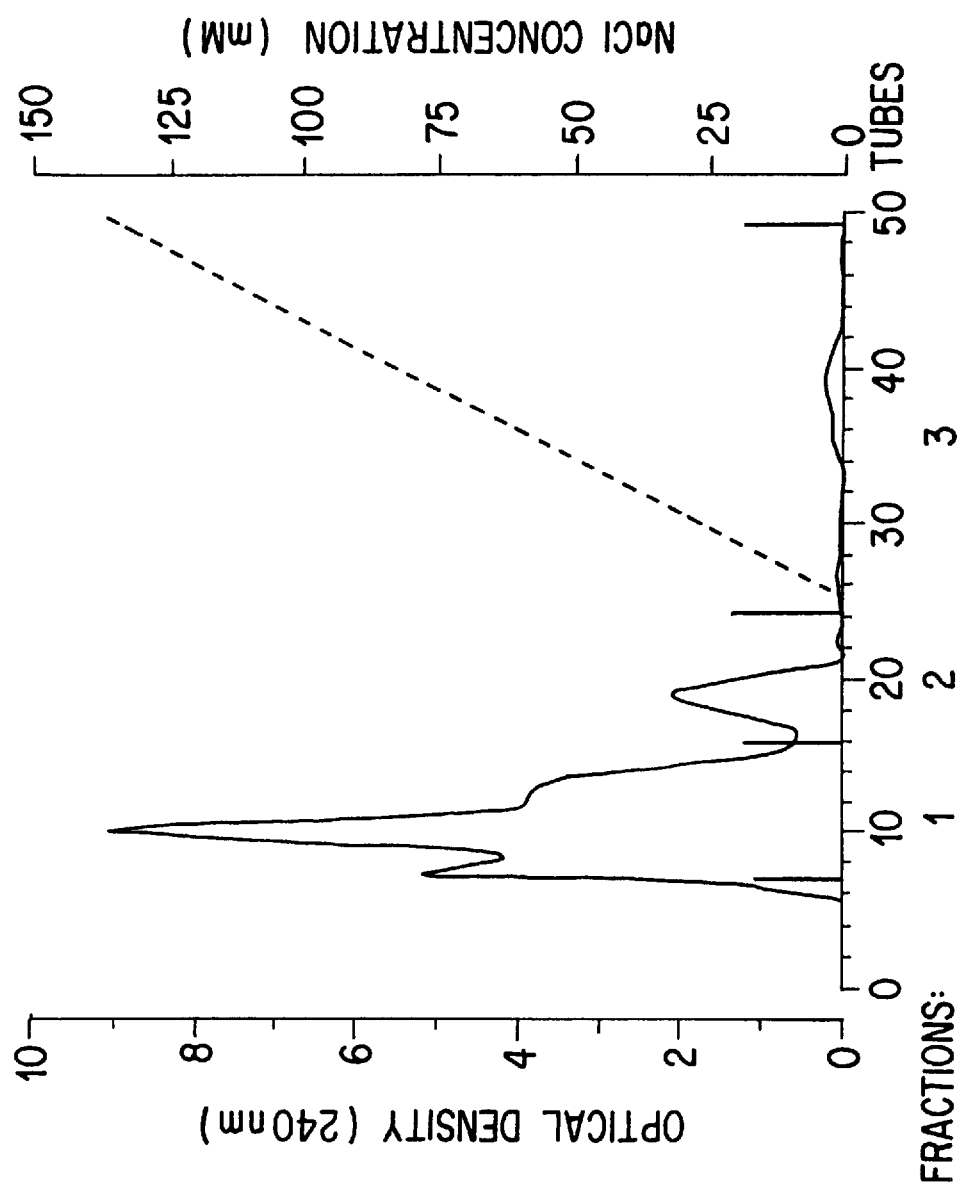

A 100 mg sample of the above fraction was loaded onto a DEAE-TSK preparative column and eluted by an NaCl gradient. The 220 nm profile of the molecules eluted defined three principal fractions (FIG. 2). After collection together, each fraction obtained by the successive injections of material was washed, concentrated and freeze-dried.

Figure 6A:
Figure 6B:
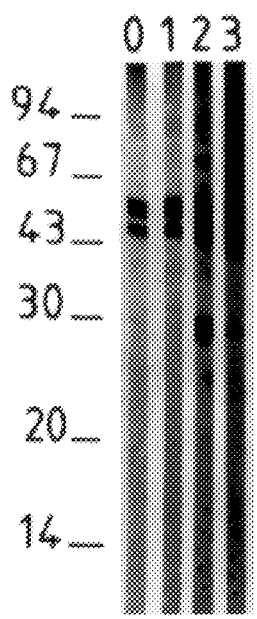
Figure 6C:
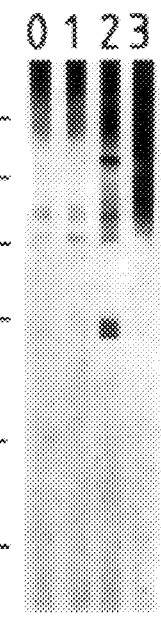
Figure 6D:
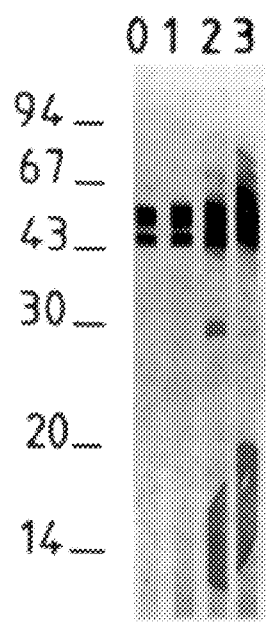
Figure 6E:
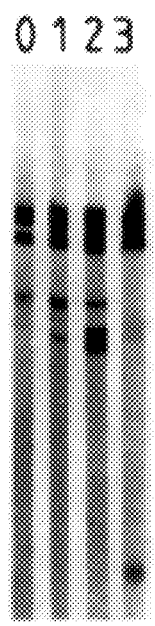

After electrophoresis on SDS gel of 5 μg of each of the above fractions, the immuno-imprints on PVDF sheets were revealed by the protein colorant (Aurodye) (FIG. 6A), by the serums from guinea-pigs immunized with live (FIG. 6B) or dead (FIG. 6C) bacilli, rabbit serum (FIG. 6D) or monoclonal antibody (FIG. 6E). The fraction 1-DEAE contained only a few antigens recognized by the antibodies from animals immunized with dead bacilli. On the other hand, this same fraction 1-DEAE contained a doublet at 45/47 kD strongly recognized by the antibodies from guinea-pigs immunized with live bacilli, as well as the rabbit serum and the monoclonal antibody. This fraction 1-DEAE was selected for the following purification stage.

4) Reversed-phase column stage:

A 10 μm RP 300 column, equilibrated with the ammonium acetate buffer (20 mM), received a 1 ml sample containing a maximum of 5 to 10 mg of the above fraction 1-DEAE. Elution with an acetonitrile gradient of 0 to 90% according to the scheme of FIG. 3 allowed recovery of five principal fractions. These fractions were concentrated by vacuum evaporation at 40° to eliminate the majority of the acetonitrile, then freeze-dried.

Fraction 4 (30–50% acetonitrile gradient) contained the majority of the molecules recognized by the antibodies from animals immunized with live bacilli or by the antibodies present in the rabbit serum or by the monoclonal antibody, and mainly these molecules after coloration of the proteins by Aurodye (FIG. 6).

EXAMPLE 3:

Cloninc and expression of the 45/47 kD proteins from *Mycobacterium tuberculosis* in *Mycobacterium smegmatis* and *Escherichia coli.*

1) Materials and methods.

1.1 Bacterial strains and growth conditions, preparation of supernatants and bacterial extracts.

*M. bovis* BCG (strain 1173$P_2$) was cultivated in Sauton's synthetic medium for 7 days at 37° C., and the supernatant was then filtered on a 0.22 μm membrane. These supernatants were then stored crude in the presence of 4% butanol or concentrated on an Amicon-PM membrane and freeze-dried.

*M. smegmatis* $mc^2$ 155 (Snapper et al., 1990, Molecular Microbiol., 4, 1911–1919) was cultivated in an 7H9+OADC liquid medium for 7 days at 37° C. Each *M. smegmatis* $mc^2$ 155 clone transformed by the cosmids from the pYUB18:*M. tuberculosis* library was cultivated in the presence of kanamycin at 25 mg/ml. The cultures were then centrifuged for 15 min at 5000 rpm, and the supernatants from the culture were separated and stored at 4° C. in the presence of 4% butanol. These preparations were used for the ELISA assays in which the composition of the medium did not interfere. When the supernatants from the clone culture were analyzed on SDS-PAGE gel, these were cultivated in Sauton's synthetic medium for 7 days at 37° C., the culture supernatants were filtered on a 0.22 μm membrane, then concentrated on an Amicon-PM10 membrane and freeze-dried.

The *E. coli* NM554 and XL 1-Blue strains were cultivated in solid or liquid Luria-Bertani (LB) medium at 37° C. The *E. coli* XL 1-Blue clones, transformed by the pUC18 plasmid, were cultivated in the presence of 25 μg/l of ampicillin.

The bacterial culture lysates of *E. coli* XL1-Blue and of each clone transformed by the recombinant pUC18: *M. tuberculosis* plasmids were prepared by a rapid freezing/thawing series at −70° C. and +60° C. of bacteria obtained after culture for one night (16 h). The lysates were centrifuged, and the supernatants separated and stored at −20° C. An analysis of the proteins from these preparations was carried out by the BCA technique (Pierce).

1.2 Cloning vectors

The gene library from *M. tuberculosis* used (Jacobs et al., 1991, cited above) was produced by electroporation in M. smegmatis $mc^2$ 155 by Stewart Cole. The applicant had 400 recombinant clones available.

The library was created in a cosmid, shuttle vector pYUB18. This latter was derived from the pYUB12 plasmid (Snapper et al., Proc. Natl. Acad. Sci. USA, 1988, 85: 6987–6991) in which the Cos sequence of the lambda bacteriophage had been inserted, enabling an amplification and good retention of the recombinant cosmids in the library in the form of phage lysates. This library had been created in the following way : the genomic DNA from M. tuberculosis strain H37Rv had been partially digested by enzyme Sau 3a, under conditions allowing a maximum of 35 kb to 45 kb fragments to be obtained. These fragments were purified then ligated in pYUB18, digested by the restriction endonuclease BamHI and dephosphorylated.

The pUC18 plasmid vector (Yanisch-Perron et al., Gene, 1985, 33: 103–119) was used for the subcloning in *E. coli* XL-Blue. This multicopy plasmid carries a DNA fragment derived from the lac operon of *E. coli* which codes for a terminal amino-fragment of beta-galactosidase. This fragment is inducible by isopropyl beta-D-thiogalactopyranoside (IPTG) and is able to establish alpha-complementation with the defective beta-galactosidase form coded by the *E. coli* XL1-Blue host strain. The insertion of foreign DNA thus induces an abolition of alpha-complementation. The recombinant plasmids can be identified when they are transformed in the host strain by the white color of the colonies, compared with the blue color of the colonies when the bacteria have been transformed by the pUC18 plasmid. This screening was carried out in the presence of IPTG and the X-Gal enzyme substrate.

1.3 Molecular biology techniques 1.3.1 Extraction of *M. smegmatis* $mc^2$ 155 cosmids The extractions of recombinant PYUB18:*M. tuberculosis* cosmids were carried by use of the alkaline lysis technique adapted for *M. smegmatis* (Jacobs et al., 1991, cited above) with some modifications. The bacteria were collected on the fifth day of culture (end of the exponential phase), and centrifuged for 10 min at 5000 rpm. The bacterial residue (3 ml) was resuspended in 5 ml of solution A (50 mM glucose, 25 mM tris HCl pH 8, 10 mM EDTA, lysozyme 10 mg/ml) and incubated at 37° C. for 20 min. Two volumes (10 ml) of solution B (0.2 N NaOH, 1% SDS) were then added and mixed by inversion. The mixture was incubated for 30 min at 65° C., then 15 min at 4° C. Finally 1.5 volumes (7.5 ml) of solution C (5 mM potassium acetate, acetic acid 11.5%) was added and mixed by inversion. The mixture was incubated for 30 min at 4° C. The preparation was then centrifuged for 15 min at 13000 rpm at 4° C., the supernatant recovered, measured and treated with the same volume of 50/50 phenol/chloroform.

After extraction, the tube was centrifuged at 4000 rpm for min. The aqueous phase was transferred into a clean tube and treated with twice the volume of ethanol stored at −20° C. After inversion, this was kept for at least 1 hour at −20° C., then centrifuged for 20 min at 12000 rpm. The residue was finally washed with one volume of 70% ethanol stored at −20° C. and dried in a Speed-Vac for 5 min. The dry residue was taken up in 500 μl of sterile water and stored at −20° C.

1.3.2 Extraction and purification of E. coli plasmids

The rapid extractions of pYUB18 cosmids and pUC18 recombinant plasmids were carried out by the alkaline lysis technique (Birnboim et al., Nucleic Acids Res., 1979, 7:1513).

The relevant cosmids and recombinant plasmids were purified after an alkaline lysis stage by ultracentrifugation on a cesium chloride gradient in the presence of ethidium bromide (Maniatis et al., Cold Spring Harbor, New York: Cold Spring Harbor Laboratory Press, 1982).

1.3.3. Transformation techniques

Chemical method with calcium chloride.

This conventional technique was used for transforming E. coli XL1-Blue by pUC18 recombinant plasmids. The competent bacteria were first prepared: 20 ml of 2YT medium were sown with a preculture for one night at 1/100. The bacteria were subjected to culture under agitation for 2 hours at 37° C. until OD=0.6, then centrifuged for 10 min at 4000 rpm at 4° C. The residue was taken up in 8 ml of 100 mM $CaCl_2$, kept for 15 min in melting ice, then centrifuged again for 10 min at 4000 rpm at 4° C. The residue was finally taken up in 1.6 ml of 100 mM $CaCl_2$, kept in melting ice for 30 min.

The competent bacteria thus prepared were freshly used for transformations or could be stored for several days at 4° C. At the moment of transformation 200 µl of competent bacteria were mixed with 2 µl of DNA. The mixture was stored for 45 min in melting ice, then subjected to thermal shock for 2 min at 42° C. 800 µl of 2YT medium were added, then the preparation was incubated for one hour at 37 with agitation, then spread onto ML-ampicillin dishes at 50 µl to 200 µl per dish. The next day the colonies were counted and the efficiency of the transformation was calculated.

Physical electroporation method.

This technique was used for transforming E. coli by large vectors: strain NM554 of E. coli was electropored by recombinant pYUB18 cosmids of size greater than 50 kb. The competent bacteria were freshly prepared: 200 ml of 2YT medium were sown with a preculture at a dilution of 1/100 for one night; the bacteria were cultivated for 3 hours at 37° C., then centrifuged at 6000 rpm for 10 min. The residue was taken up in 10 ml of sterile water at 4° C., then in 190 ml of sterile water at 4° C. The bacteria were again centrifuged at 6000 rpm for 10 min and rewashed with 10 ml of sterile water at 4° C. Finally the residue was taken up in 400 µl of 10% glycerol.

The electroporation was carried out on a Bio-Rad Gene Pulser. 100 µl of bacteria were mixed with 1 to 4 µl of DNA in a 0.4 mm cell. The mixture was subjected to electrical shock (2500 volts, 25 µF), then 1 ml of 2YT medium was rapidly added to the cell. The whole was transferred into a tube and incubated for 1 hour at 37° C. with agitation. After incubation the culture was spread onto ML-ampicillin dishes at 50 µl to 200 µl per dish. The next day the colonies were counted and the efficiency of the transformation was calculated.

1.3.4 Cloning of fragments from enzymatic digestion

The DNA to be cloned was digested by a BamHI restriction endonuclease. The PUCIS plasmid was digested in the same way. The fragments resulting from the required pYUB18 recombinant cosmid were ligated in the plasmid vector by the activity of the T4 DNA ligase enzyme (Amersham). Ligation was carried out in a 20 µl volume at 16° C. overnight. The whole of the ligation mixture was used for transformation in E. coli XL1-Blue. After phenotypic expression, all the bacteria were spread on ML-ampicillin plates at 25 µg/ml, IPTG, X-Gal. The recombinant clones not permitting alpha-complementation were located from the white color of these colonies.

The recombinant clones were studied after purification by cloning. The plasmid DNA was extracted by alkaline lysis then analyzed on 0.8% agarose gel before or after digestion with restriction endonuclease BamH I.

1.3.5 Production of a restriction map

The pLA34 and pLA4 recombinant plasmids, containing a 3 kb BamH I-BamH I insert cloned in both directions, were digested by the different restriction endonucleases having a site in the pUC18 multisite linker (polylinker). Single and double digestions were carried out by use of the restriction endonucleases BamH I, Hind III, Sph I, Xba I, Sal I, Kpn I EcoR I, and Sma I, then analyzed on 0.8% agarose gel. After coloration of the DNA with ethidium bromide the size of the different fragments was determined as a function of their migration distance compared with the markers (an internal laboratory standard, pKN plasmid digested by Pvu II).

1.4 Methods of protein detection

1.4.1 ELISA technique

A competitive ELISA test was used for measuring the concentration of the 45/47 kDa proteins in the different preparations obtained from bacterial cultures, by use of a polyclonal serum (Romain et al., 1993, cited above).

This polyclonal rabbit serum was obtained against the 45/47 proteins by a conventional immunization technique: injection of 50 µg of purified proteins in incomplete Freund's adjuvant and of 25 µg one month later.

The wells of a first microplate were covered either by purified proteins in solution at a concentration of 1 µg/ml in carbonate buffer or by a 15 day *Mycobacterium bovis* BCG supernatant at a concentration of 10 µg/ml. The antigen fixation was carried out for one hour at 37° C., and the microplate was then washed five times with PBS. In a second incubation the wells were saturated with a solution of PBS, 0.5% gelatin, 4% butanol for one hour at 37° C. The microplate was then washed 5 times with PBS-Tween 0.1%.

The test was carried out as follows:

Incubation in a second microplate of 50 µl of the supernatant to be analyzed at different dilutions (pure, ½, ¼, ⅛, etc.) in PBS-Tween 0.1%, 0.25% gelatin, 4% butanol, and of 50 µl of rabbit serum prepared at a dilution of 1/4000 in PBS-Tween 0.1%, 0.25% gelatin, 4% butanol, for one hour at 37° C., then transfer of the mixture onto the first microplate and incubation for one hour at 37° C. The microplate was then washed 10 times with 0.1% PBS-Tween. Finally an anti IgG H+L anti-rabbit conjugated antibody (Biosys), marked with alkaline phosphatase, prepared at a dilution of 1/4000 in PBS-Tween 0.1%, 0.25% gelatin, 4% butanol, was incubated for one hour at 37° C. The microplate was washed 10 times with PBS-Tween 0.1%.

The enzyme substrate, para-nitrophenyl phosphate (pNPP) was finally incubated at a concentration of 40 mg/24 ml in a $NaHCO_3$, $MgCl_2$, pH 9.6 buffer for one hour or overnight. The OD were read at 414 nm and 690 nm on a Titerteck Twinreader.

1.4.2 Immuno-imprint technique

The conventional gel-electrophoresis technique on denaturing SDS-PAGE gel was used (Laemmli, Nature, 1970, 277: 680–685), followed by an electrotransfer on a PVDF membrane (Towbin et al., Proc. Natl. Acad. Sci. USA, 1979, 76: 4350–4354; Pluskal et al., Biotechniques, 1986, 4: 272–283).

The samples analyzed on gel were measured quantitatively; in µg of lyophilizate for the *M. smegmatis* supernatants (5 µg were applied) and in µg of proteins for the *E. coli* lysates (25 µg were applied).

The purified M. bovis BCG proteins were placed on the gel at a concentration of 0.25 μg of protein per track.

The proteins transferred on the membrane were revealed by rabbit polyclonal serum at a dilution of 1/500th for the proteins expressed in the mycobacteria.

In order to reveal the recombinant proteins in E. coli, these polyclonal antibodies were purified on a DEAE (Trisacryl$^D$) column, and the immunoglobulins obtained then absorbed on an E. coli lysate immobilized on a Sepharose-4B column activated by cyanogen bromide (Pharmacia) (Maniatis et al., 1982). The non-retained antibodies were stored in a pool at 4° C. then used for revealing the proteins transferred on the membrane at a dilution of 1/100th.

An anti-Ig H+L conjugate (Bio-Sys), species-specific, marked by alkaline phosphatase, was used for revealing the above antibodies at a dilution of 1/3000. Finally the alkaline phosphatase activity was revealed by two artificial chromogenic substrates: tetrazolium blue and 5-bromo-4-chloro-3-indolyl phosphate.

1.5 DNA sequencing

The nucleotide sequencing was carried out by use of a group of clones obtained by different deletions from the two clones pLA34 and pLA4. The deletions were selected according to the restriction map established.

The sequencing was performed from double-stranded plasmid DNA matrices. Sanger's technique was applied by use of a T7 Sequencing kit (Pharmacia) and $^{35}$ATP.

The sequence was obtained by use of different deleted clones and universal primers (Direct and Reverse Primers) of the pUC18 plasmid, then synthetic oligonucleotides.

The sequences were established on the two complementary strands.

The compression zones resulting from the high percentage of GC in the genomic DNA of M. tuberculosis (65%) were sequenced with the aid of a T7 Deaza G/A Sequencing kit (Pharmacia) containing 7-Deaza dGTP, a chemical analogue of dGTP.

1.6 Sequence analysis:

The comparisons and assemblies of the contiguous sequences obtained were carried out with the help of the STADEN program on Unix. The sequence homologies searched for among the sequences of the EMBL and GenBank data banks were made by use of the FASTA and T-FASTA programs of GCG.

2) Results 2.1 Cloning and expression of the 45/47 kDa proteins from M. tuberculosis in M. smegmatis.

2.1.1 Screening of a gene library for expression of M. tuberculosis in M. smegmatis.

The gene library used (Jacobs et al., 1991, cited above) was created by cloning the 40 kb fragments resulting from a partial genome digestion by the restriction endonuclease Sau 3a in the pYUB18 cosmid vector. The size of the genome, estimated by pulsed field electrophoresis at 4200 kb, is thus contained in approximately 100 to 150 clones.

A competitive ELISA test was used to determine the proteins in liquid medium (Romain et al., 1993, cited above). It enabled the detection and definition of the quantity of the 45/47 kDa proteins in the supernatant from 7 day cultures of M. bovis BCG (FIG. 8).

This test has the following advantages: good sensitivity, that is the ability to detect a quantity of the order of 1 ng/ml of proteins in liquid medium by use of a polyclonal serum diluted to 1/8000th (Romain et al., 1993, cited above) and ease of operation for rapidly screening a series of samples.

A series of 400 pYUB18::M. tuberculosis H37Rv recombinant clones, electropored in M. smegmatis, was screened.

For this, the different clones were cultivated for 7 days in 7H9+OADC medium. The recombinant proteins were searched for in the test by analyzing the supernatants obtained after centrifuging the cultures.

Three clones were found which were able to express the proteins recognized by the specific monoclonal antibodies of the M. bovis BCG 45/47 kDa proteins (FIG. 8). During this first screening the wells of the microtitration plates were covered by a supernatant of M. bovis BCG culture in which the 45/47 kDa proteins had been evaluated at 2% of the total mass. The three clones selected were confirmed in a second experiment in which the wells of the microtitration plates were covered by the purified 45/47 kba proteins.

2.1.2 Genetic analysis of the selected recombinant plasmids.

In order to study the different cosmids selected, these were electropored in E. coli NM554 after extraction of the M. smegmatis DNA by modified alkaline lysis. Mycobacterial extrachrosomal DNA is in fact difficult to obtain owing on the one hand to the complexity of the cell wall, which is difficult to lyse, and to the low number of vector copies which has been determined as 3 to 10 on average per bacterium. The three clones transformed in E. coli NM554 were isolated on ML-kanamycin dishes, and the cosmid DNA, extracted by alkaline lysis, was analyzed on 0.8% agarose gel.

Figure 9:
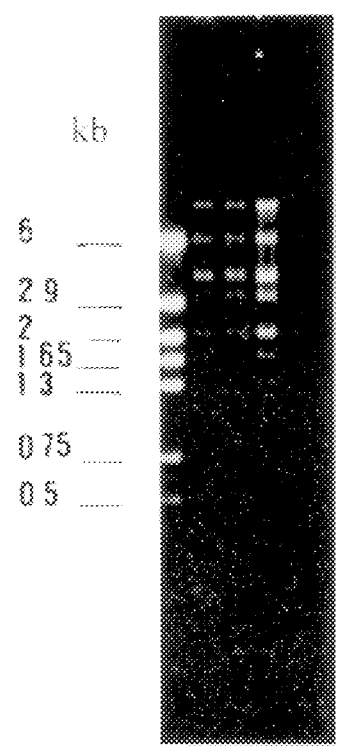

The three clones had a DNA of size greater than 50 kb. Digestion by restriction endonuclease BamH I was carried out to differentiate the profiles of these three selected cosmids. These were revealed to be identical (FIG. 9). The profiles showed a 12 kb band corresponding to the PYUB18 vector, then a series of bands of lower molecular weight corresponding to the cloned DNA fragment (approximately 40 kb). Taking account of the number of bands obtained and their location on the gel, it could be considered that the cosmids isolated were identical.

Figure 10:
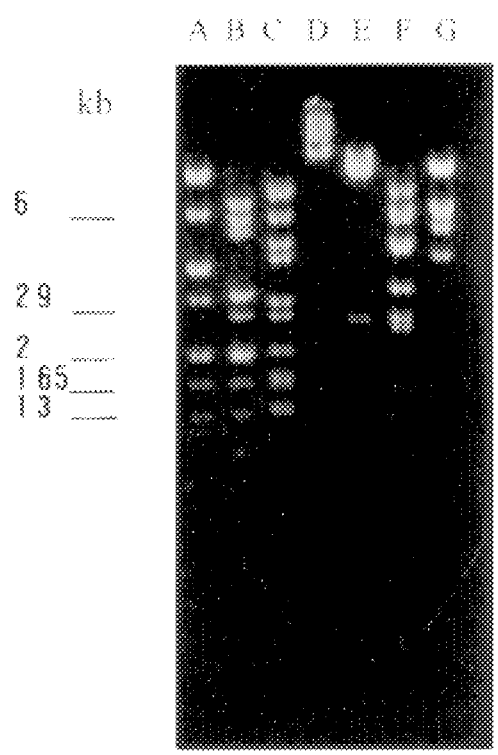

Different digestions of the pLA1 cosmid alone were carried out by restriction endonucleases with more or less frequent cleavage sites for a DNA rich in G+C in order to differentiate the fragments with medium length, sufficient to contain the gene or genes for the 45/47 kDa proteins, and to carry out a sub-cloning of these (FIG. 10).

2.1.3 Expression of the 45/47 kDa proteins from M. tuberculosis in M. smegmatis.

The pLA1 cosmid containing an insert of approximately 40 kb allowed the expression of recombinant proteins in M. smegmatis, detected in a culture supernatant by polyclonal antibodies.

Figure 11:
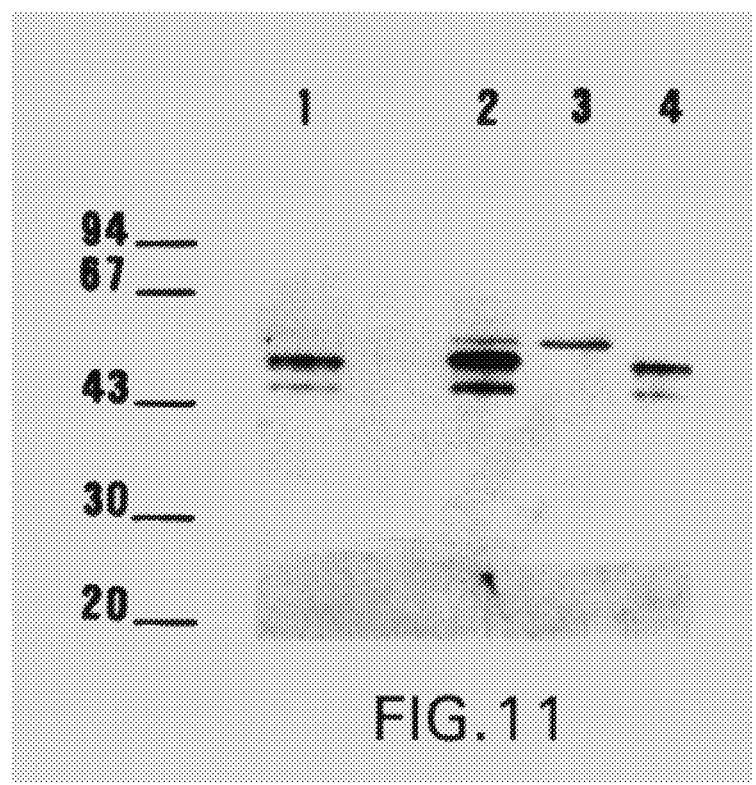

In order to determine the approximate sizes of the proteins expressed, a freeze-dried supernatant from a 7 day culture was analyzed by immuno-imprint. The recombinant proteins expressed in M. smegmatis had two molecular weights of 45/47 kDa apparently identical to those expressed in M. bovis BCG (FIG. 11).

Figure 12:
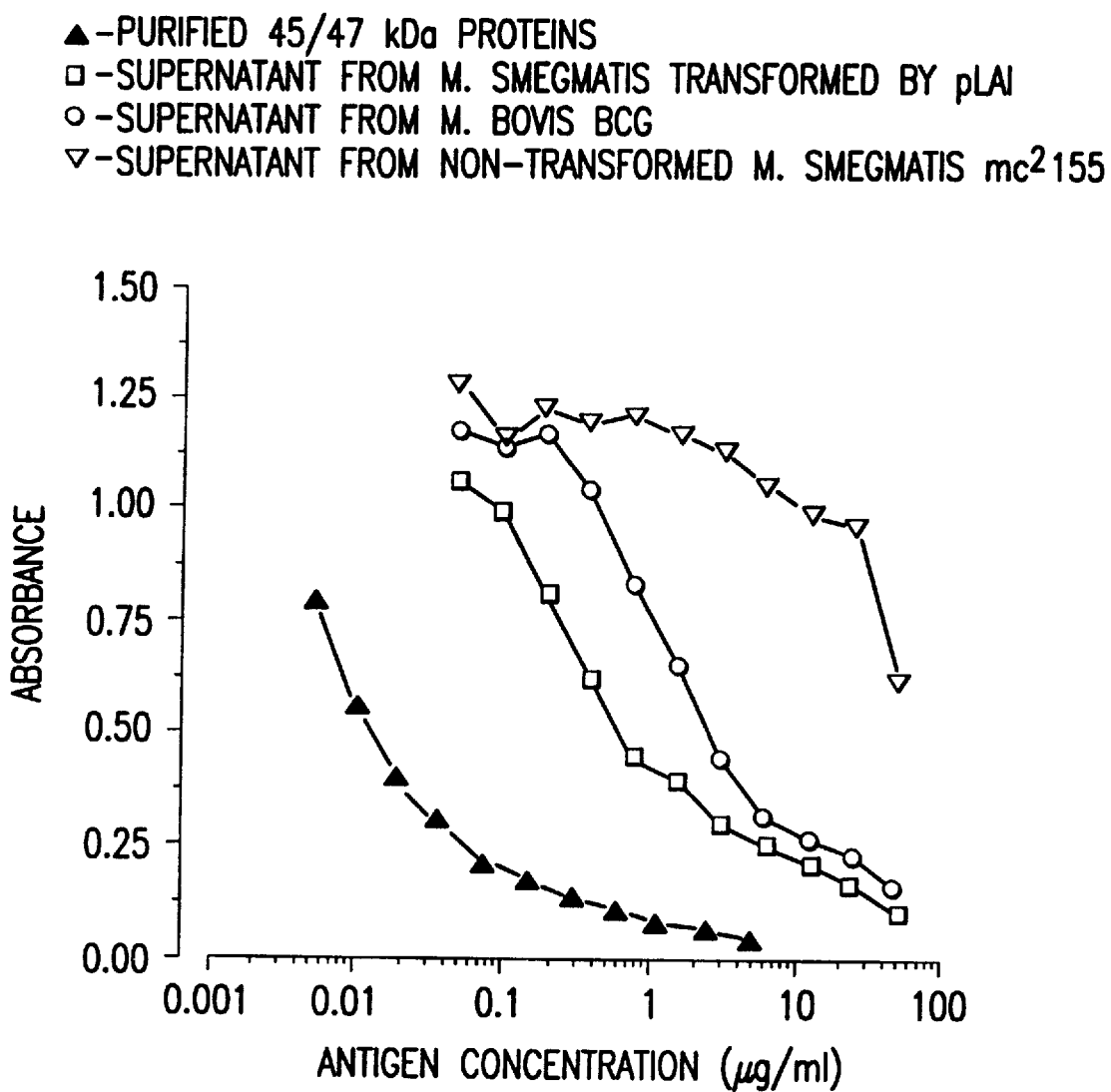

In another experiment, the level of expression of these recombinant proteins was compared to that in M. bovis BCG. A measured quantity of proteins from freeze-dried supernatants was used during a determination by a competitive ELISA test. Different concentrations of lyophilized supernatants were revealed with a 1/8000th dilution of rabbit polyclonal serum. Recombinant M. smegmatis allowed the expression of the proteins in quantities 5 times greater than for M. bovis BCG (FIG. 12).

A sub-cloning of this insert, together with an analysis of the recombinant proteins in the heterologous host (E. coli), was carried out in order to determine the number of genes coding for these proteins.

2.2 Cloning and expression of the 45/47 kDa proteins from M. tuberculosis in E. coli.

2.2.1 Sub-cloning and expression of the 45/47 kDa proteins in E. coli.

When pLA1 had been transformed in a heterologous host E. coli NM554, no recombinant protein was detected in the supernatants from the bacterial cultures or lysates. In order to favor the expression of these proteins, a sub-cloning of the fragments resulting from a BamH I digestion of the cosmid was carried out in the pUC18 plasmid (Yanisch-Perron et al., Gene, 1985, 33: 103, 119).

The pUC18::M. tuberculosis recombinant plasmids transformed in E. coli XL1-Blue were selected by lack of beta-galactosidase expression of the host bacteria. The plasmid DNA of each "white" clone from a series of 36 clones) was prepared by alkaline lysis and digested by restriction endonuclease BamH I.

Figure 13A:
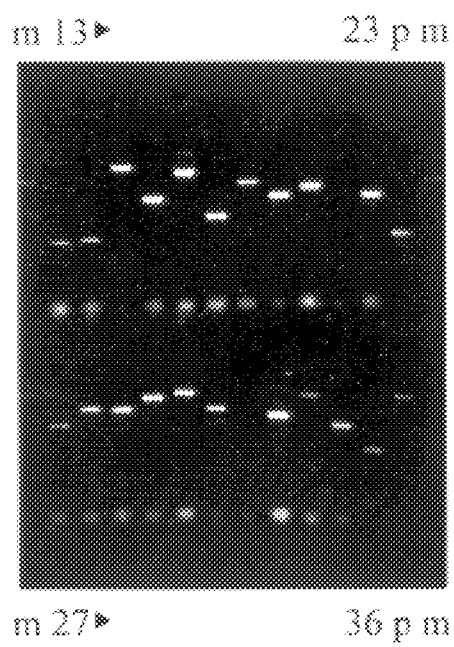

The size of the plasmids obtained observed in agarose gel showed several profiles indicating that the recombinant plasmids were different (FIG. 13A).

Figure 13B:
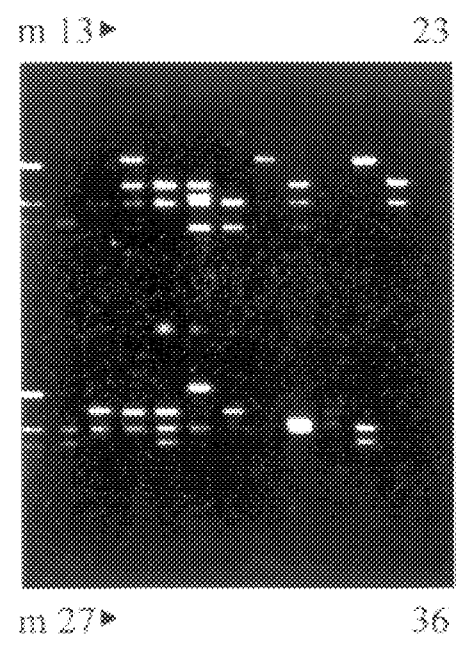

The size of the cloned inserts also observed in agarose gel showed different restriction profiles (FIG. 13B). These profiles all showed a 2.8 kb fragment corresponding to the pUC18 vector and a series of fragments of different sizes corresponding to the cloned inserts.

All the digestion fragments were cloned alone, in twos or in threes, except for the 12 kb fragment which was difficult to clone because of its large size.

The 36 clones selected were screened for their ability to induce the expression of recombinant proteins in E. coli XL1-Blue. This experiment was carried out in the same competitive ELISA test as before.

No recombinant protein was detected in the bacterial culture supernatants. On the other hand recombinant proteins were detected in the bacterial lysates of clones containing at least one 3 kb insert.

The level of expression of the proteins measured in the test seemed to be influenced by the size of the plasmids. Among the 36 clones studied, 2 clones were found to allow expression, pLA34 and pLA35, containing 3 kb and 7 kb inserts respectively. This was greatest for pLA34 as shown by the results in table 1 (see below).

2.2.2 Restriction map of the pLA34 and pLA34-2 clones.

Figure 14:
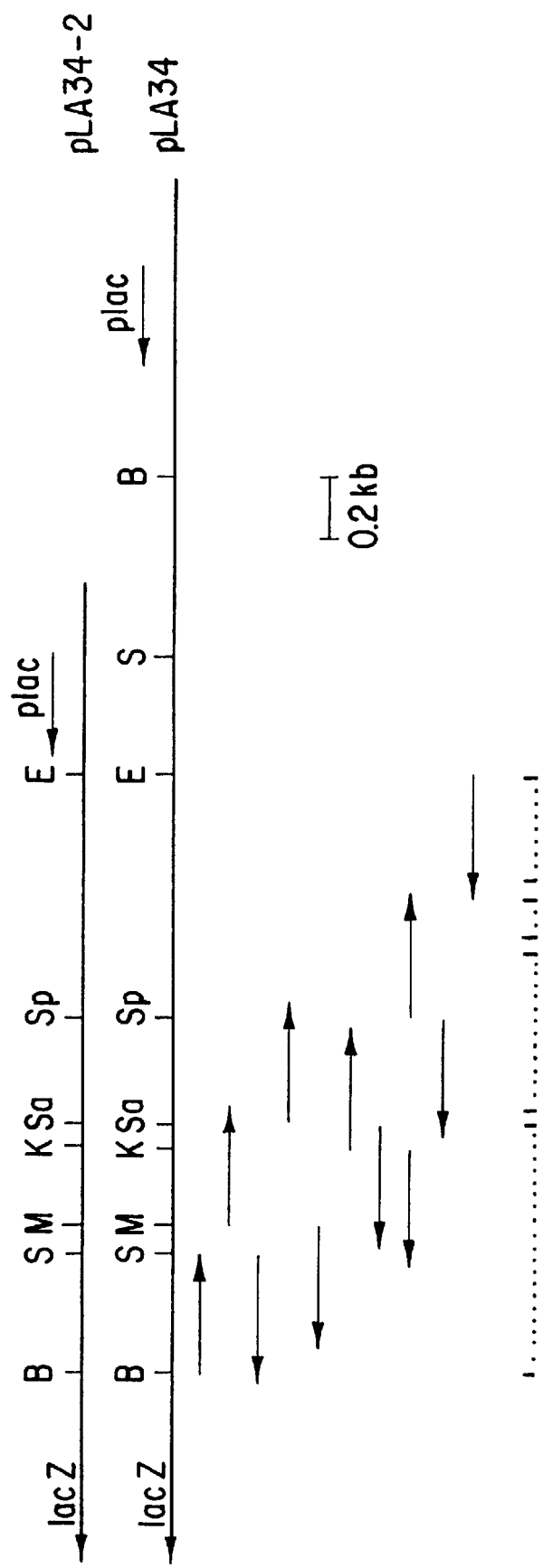

A restriction map for the pLA34 plasmid was established, identifying different cleavage sites for current restriction endonucleases, present in the multisite linker (polylinker) of pUC18 (FIG. 14). A single restriction site EcoR I separated the 3 kb insert into two fragments of 2 kb and 1 kb.

Figure 15:
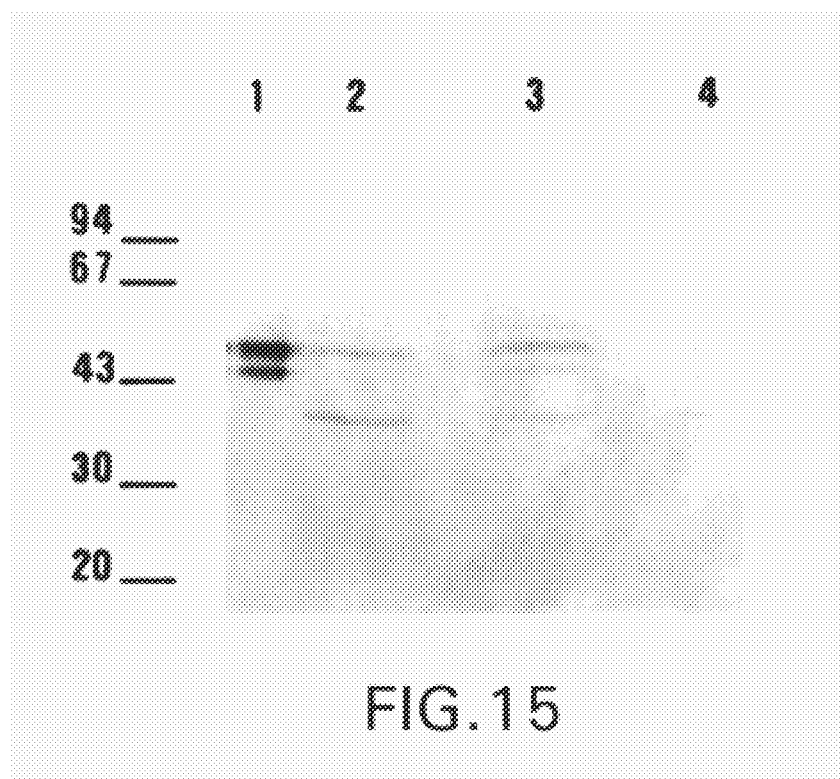

The pLA34-2 clone having a 2 kb BamH I-EcoR I insert was produced from the above clone by deletion. This also allowed expression of recombinant proteins in the bacterial lysates (FIG. 15).

Figure 16:
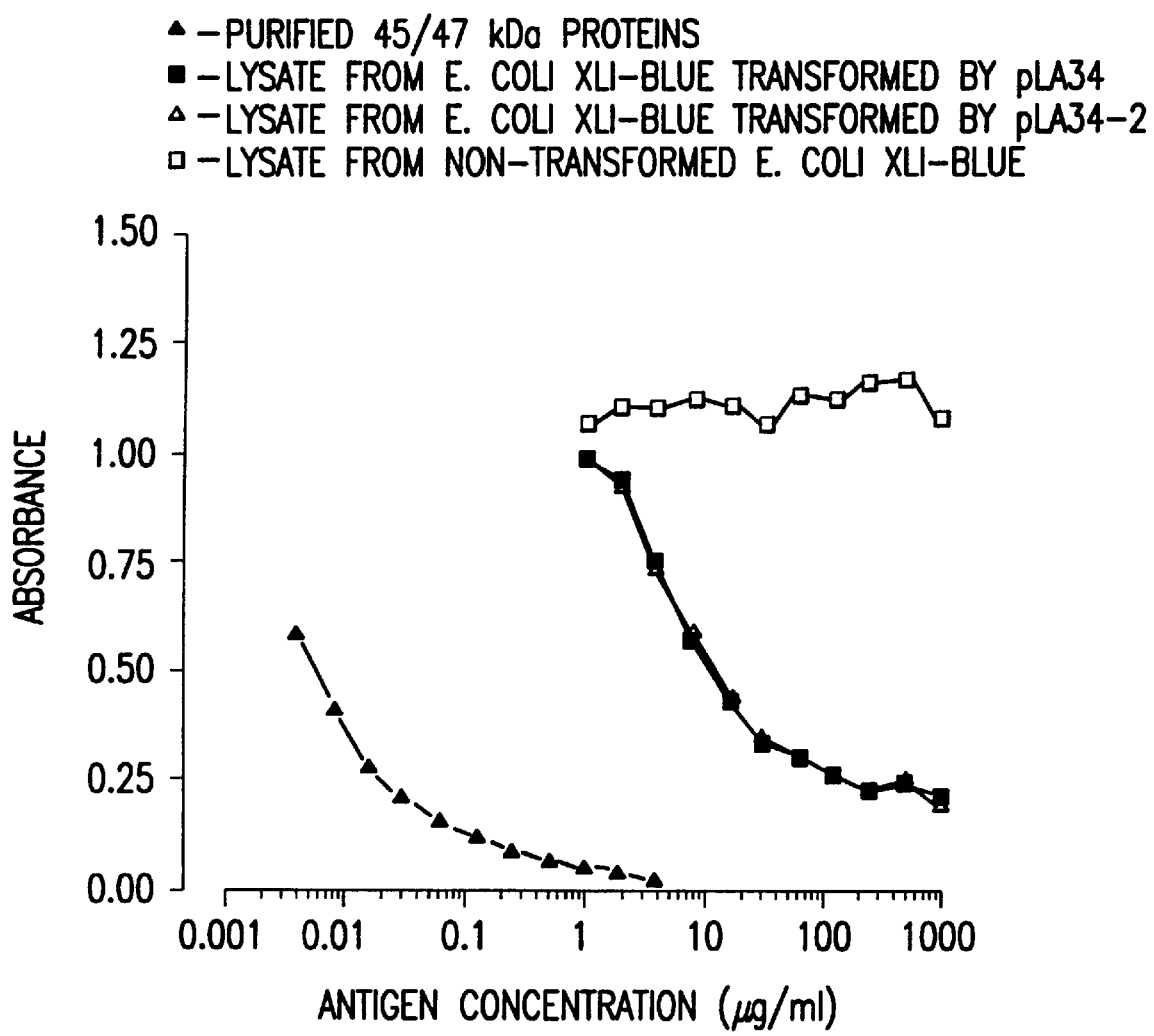
FIG. 16 illustrates the expression of the 45/47 kDa proteins in E. coli. The bacterial culture lysates, analyzed by a competitive ELISA assay, were used in the crude form.

Immuno-imprint analysis of the bacterial lysates showed proteins with two molecular weights of 45 and 47 kDa, apparently identical to the native proteins expressed in M. bovis BCG (FIG. 16).

2.2.3 Analysis of the nucleotide sequence coding for the 45/47 kDa proteins of M. tuberculosis H37Rv:

The complete nucleotide sequence of the gene coding for the 45/47 kDa proteins, the upstream sequence and the sequence deduced from amino acids, are shown in sequences SEQ ID NO: 1 and SEQ ID NO: 2. The single gene permitting the expression of the protein doublet has 975 base pairs between positions 1082 and 2056, inclusive, of the nucleotide sequence.

A consensus sequence for ribosome fixation (Shine Dalgarno) was identified upstream of the gene.

The gene has a high percentage of GC of 69.4% compared with 65% of GC for M. tuberculosis.

The protein deduced from the gene has a typical signal sequence with an ANA cleavage site for the signal peptidase.

The gene codes for a protein with 325 amino acids which includes a signal sequence of 39 amino acids.

The results obtained by biochemical analysis of the amino acid composition of the purified proteins from M. bovis BCG and M. tuberculosis compared with those deduced from the protein sequence are in good agreement (table 2). This leads to the conclusion that there is a single gene which allows the expression of proteins of two molecular weights in Mycobacterium smegmatis and E. coli.

2.2.4 Analysis of the protein sequence and comparison of sequences:

The molecular weight calculated from the deduced amino acid sequence is 28.7 kDa.

The calculated isoelectric point is 4.36. This last result is also in good agreement with biochemical determination of the isoelectric point carried out on purified M. bovis BCG proteins.

The deduced amino acid sequence shows a high percentage of proline and alanine (21.8% and 19.1%).

The complete sequence shows a homology with a recently described protein from Mycobacterium leprae. The two sequences are compared in FIG. 17. The homology score between the two proteins is 65.4%. This protein described for Mycobacterium leprae also has a signal sequence typical for secreted proteins.

Figure 18:
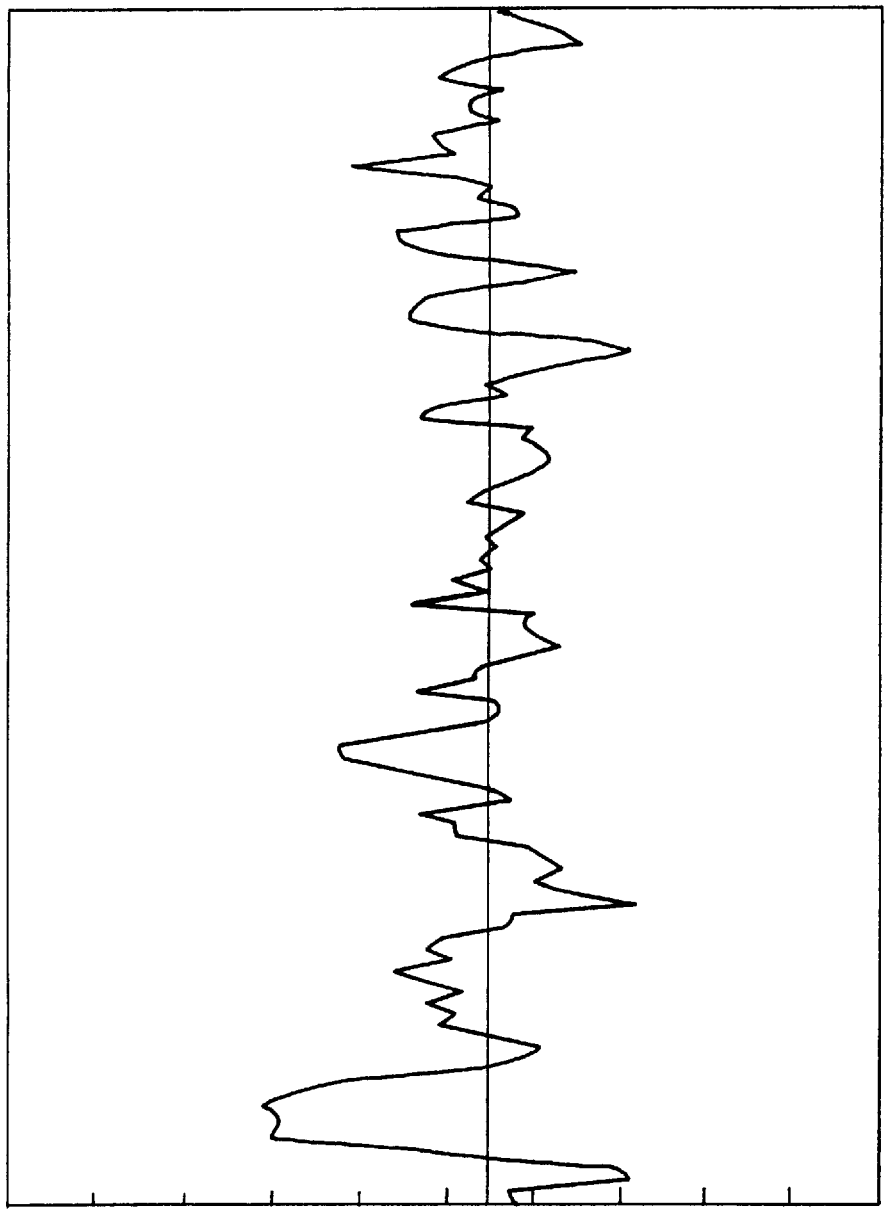
FIG. 18 is a hydrophobicity profile of the protein of sequence SEQ ID NO: 2.

The hydrophobicity profile of the protein deduced from M. tuberculosis, which is the object of the present invention (SEQ ID NO: 2) has been established. It is shown in FIG. 18.

TABLE 1

Cloning in pUC18 of a 3 kb insert allowing expression of recombinant proteins in E. coli

| pUC18: M. tuberculosis clones | Size of inserts | ELISA expression of proteins |
|---|---|---|
| N° 34 | 3 kb | ++ |
| N° 35 | 3 kb + 4 kb | + |
| N° 4 | 3 kb | − |
| N° 17 | 3 kb + 4 kb + 1.7 kb | − |

TABLE 2

Amino acid compositions of the 45/47 kDa proteins from M. tuberculosis and M. bovis BCG and of 27/32 kDa proteins from M. leprae

| | Sequence deduced (% in moles) | | Chemical analysis (% in moles) | |
|---|---|---|---|---|
| Residue | M. leprae | M. tuber | M. tuber | M. bovis BCG |
| A = Ala | 13.3 | 18.5 | 19.2 | 19.2 |
| B = Asx | — | — | 10.4 | 10.6 |
| C = Cys | 0.4 | 0 | <0.5 | <0.5 |
| D = Asp | 4.8 | 5.2 | — | — |
| E = Glu | 4.8 | 3.1 | — | — |
| F = Phe | 2.0 | 2.5 | 2.4 | 2.2 |
| G = Gly | 8.0 | 7.0 | 7.1 | 7.4 |
| H = His | 0.8 | 0.3 | 0.4 | 0.4 |
| I = Ile | 5.2 | 2.5 | 2.2 | 2.3 |
| K = Lys | 2.8 | 2.5 | 2.7 | 2.9 |
| L = Leu | 6.8 | 4.2 | 4.4 | 4.7 |
| M = Met | 0.8 | 0.7 | 0.5 | 0.5 |
| N = Asn | 4.0 | 4.5 | — | — |
| P = Pro | 13.3 | 21.7 | 20.9 | 21.9 |
| Q = Gln | 3.2 | 2.8 | — | — |
| R = Arg | 2.8 | 2.8 | 2.7 | 2.5 |
| S = Ser | 9.6 | 5.9 | 5.6 | 5.0 |
| T = Thr | 4.8 | 6.3 | 5.7 | 5.4 |
| V = Val | 8.0 | 5.9 | 6.2 | 5.8 |
| W = Trp | 1.2 | 1.4 | N.D. | N.D. |

TABLE 2-continued

Amino acid compositions of the 45/47 kDa proteins from *M. tuberculosis* and *M. bovis* BCG and of 27/32 kDa proteins from *M. leprae*

| Residue | Sequence deduced (% in moles) | | Chemical analysis (% in moles) | |
| --- | --- | --- | --- | --- |
| | *M. leprae* | *M. tuber* | *M. tuber* | *M. bovis* BCG |
| Y = Tyr | 2.8 | 2.1 | 2.2 | 2.2 |
| Z = Glx | — | — | 6.3 | 6.0 |

\* Asx = Asp + Asn
Glx = Glu + Gln

---

We claim:

1. A composition of matter comprising a purified recombinant protein which comprises the contiguous amino acid sequence of SEQ ID NO:3.

2. The composition of claim 1, wherein the purified recombinant protein consists of SEQ ID NO: 3.

3. A kit comprising the composition of claim 1.

4. A composition comprising a protein which is obtained by a process comprising culturing a transformed microorganism expressing SEQ ID NO: 1 in a culture medium and isolating the protein from the culture medium.

5. The composition of claim 4, wherein the protein comprises SEQ ID NO: 3.

6. The composition of claim 4, wherein the protein consists of SEQ ID NO: 3.

7. A kit comprising the composition of claim 4.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 2061 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: CDS
( B ) LOCATION:1082..2057

( x i ) SEQUENCE DESCRIPTION: SEQ ID NO: 1:

```
GTGCTCGGGC CCAACGGTGC GGGCAAGTCC ACCGCCCTGC ATGTTATCGC GGGGCTGCTT    60
CGCCCCCGAC GCGGGCTTGG TACGTTTGGG GGACCGGGTG TTGACCGACA CCGAGGCCGG   120
GGTGAATGTG GCGACCCACG ACCGTCGAGT CGGGCTGCTG TTGCAAGACC CGTTGTTGTT   180
TCCACACCTG AGCGTGGCCA AAAACGTGGC CTTCGGACCA CAATGCCGTC GCGGGATGTT   240
TGGGTCCGGG CGCGCGCTAG GACAAGGGCG TCGGCACTGC GATGGCTGCG CGAGGTGAAC   300
GCCGAGCAGT TCGCCGACCG TAAGCCTCGT CAGCTATCCG GGGGCCAAGC CCAGCGCGTC   360
GCCATCGCGC GAGCGTTGGC GGCCGAACCG GATGTGTTGC TGCTCGACGA GCCGCTGACC   420
GGACTCGATG TGGCCGCGGC CGCGGGTATC CGTTCGGTGT TGCGTAGTGT CGTCGCGAGG   480
AGCGGTTGCG CGGTAGTCCT GACGACCCAT GACCTGCTGG ACGTGTTCAC GCTGGCCGAC   540
CGGGTATTGG TGCTCGAGTC CGGCACGATC GCCGAGATCG GCCCGGTTGC CGATGTGCTT   600
ACCGCACCTC GCAGTCGTTT CGGAGCCCGT ATCGCCGGAG TCAACCTGGT CAATGGGACC   660
ATTGGTCCGG ACGGCTCGCT GCGCACCCAG TCCGGCGCCC ACTGGTACGG CACCCCGGTC   720
CAGGATTTGC CTACTGGGCA TGAGGCAATC GCGGTGTTCC CGCCGACGGC GGTGGCGGTG   780
TATCCGGAAC CGCCGCACGG AAGCCCGCGC AATATCGTCG GGCTGACGGT GGCGGAGGTG   840
```

```
GATACCCGCG GACCCACGGT CCTGGTGCGC GGGCATGATC AGCCTGGTGG CGCGCCTGGC        900

CTTGCCGCAT GCATCACCGT CGATGCCGCC ACCGAACTGC GTGTGGCGCC CGGATCGCGC        960

GTGTGGTTCA GCGTCAAGGC GCAGGAAGTG GCCCTGCACC CGGCACCCCA CCAACACGCC       1020

AGTTCATGAG CCGACCCGCG CCGTCCTTGC GTCGCGCCGT TAACACGGTA GGTTCTTCGC       1080
```

```
C ATG CAT CAG GTG GAC CCC AAC TTG ACA CGT CGC AAG GGA CGA TTG           1126
  Met His Gln Val Asp Pro Asn Leu Thr Arg Arg Lys Gly Arg Leu
   1               5                  10                  15

GCG GCA CTG GCT ATC GCG GCG ATG GCC AGC GCC AGC CTG GTG ACC GTT        1174
Ala Ala Leu Ala Ile Ala Ala Met Ala Ser Ala Ser Leu Val Thr Val
                     20                  25                  30

GCG GTG CCC GCG ACC GCC AAC GCC GAT CCG GAG CCA GCG CCC CCG GTA        1222
Ala Val Pro Ala Thr Ala Asn Ala Asp Pro Glu Pro Ala Pro Pro Val
                 35                  40                  45

CCC ACA ACG GCC GCC TCG CCG CCG TCG ACC GCT GCA GCG CCA CCC GCA        1270
Pro Thr Thr Ala Ala Ser Pro Pro Ser Thr Ala Ala Ala Pro Pro Ala
             50                  55                  60

CCG GCG ACA CCT GTT GCC CCC CCA CCA CCG GCC GCC GCC AAC ACG CCG        1318
Pro Ala Thr Pro Val Ala Pro Pro Pro Ala Ala Ala Asn Thr Pro
         65                  70                  75

AAT GCC CAG CCG GGC GAT CCC AAC GCA GCA CCT CCG CCG GCC GAC CCG        1366
Asn Ala Gln Pro Gly Asp Pro Asn Ala Ala Pro Pro Pro Ala Asp Pro
 80              85                  90                  95

AAC GCA CCG CCG CCA CCT GTC ATT GCC CCA AAC GCA CCC CAA CCT GTC        1414
Asn Ala Pro Pro Pro Pro Val Ile Ala Pro Asn Ala Pro Gln Pro Val
             100                 105                 110

CGG ATC GAC AAC CCG GTT GGA GGA TTC AGC TTC GCG CTG CCT GCT GGC        1462
Arg Ile Asp Asn Pro Val Gly Gly Phe Ser Phe Ala Leu Pro Ala Gly
             115                 120                 125

TGG GTG GAG TCT GAC GCC GCC CAC TTC GAC TAC GGT TCA GCA CTC CTC        1510
Trp Val Glu Ser Asp Ala Ala His Phe Asp Tyr Gly Ser Ala Leu Leu
             130                 135                 140

AGC AAA ACC ACC GGG GAC CCG CCA TTT CCC GGA CAG CCG CCG CCG GTG        1558
Ser Lys Thr Thr Gly Asp Pro Pro Phe Pro Gly Gln Pro Pro Pro Val
 145                 150                 155

GCC AAT GAC ACC CGT ATC GTG CTC GGC CGG CTA GAC CAA AAG CTT TAC        1606
Ala Asn Asp Thr Arg Ile Val Leu Gly Arg Leu Asp Gln Lys Leu Tyr
 160                 165                 170                 175

GCC AGC GCC GAA GCC ACC GAC TCC AAG GCC GCG GCC CGG TTG GGC TCG        1654
Ala Ser Ala Glu Ala Thr Asp Ser Lys Ala Ala Ala Arg Leu Gly Ser
                 180                 185                 190

GAC ATG GGT GAG TTC TAT ATG CCC TAC CCG GGC ACC CGG ATC AAC CAG        1702
Asp Met Gly Glu Phe Tyr Met Pro Tyr Pro Gly Thr Arg Ile Asn Gln
                 195                 200                 205

GAA ACC GTC TCG CTC GAC GCC AAC GGG GTG TCT GGA AGC GCG TCG TAT        1750
Glu Thr Val Ser Leu Asp Ala Asn Gly Val Ser Gly Ser Ala Ser Tyr
             210                 215                 220

TAC GAA GTC AAG TTC AGC GAT CCG AGT AAG CCG AAC GGC CAG ATC TGG        1798
Tyr Glu Val Lys Phe Ser Asp Pro Ser Lys Pro Asn Gly Gln Ile Trp
 225                 230                 235

ACG GGC GTA ATC GGC TCG CCC GCG GCG AAC GCA CCG GAC GCC GGG CCC        1846
Thr Gly Val Ile Gly Ser Pro Ala Ala Asn Ala Pro Asp Ala Gly Pro
 240                 245                 250                 255

CCT CAG CGC TGG TTT GTG GTA TGG CTC GGG ACC GCC AAC AAC CCG GTG        1894
Pro Gln Arg Trp Phe Val Val Trp Leu Gly Thr Ala Asn Asn Pro Val
                 260                 265                 270

GAC AAG GGC GCG GCC AAG GCG CTG GCC GAA TCG ATC CGG CCT TTG GTC        1942
Asp Lys Gly Ala Ala Lys Ala Leu Ala Glu Ser Ile Arg Pro Leu Val
                 275                 280                 285
```

```
GCC  CCG  CCG  CCG  GCG  CCG  GCA  CCG  GCT  CCT  GCA  GAG  CCC  GCT  CCG  GCG    1990
Ala  Pro  Pro  Pro  Ala  Pro  Ala  Pro  Ala  Pro  Ala  Glu  Pro  Ala  Pro  Ala
          290                     295                     300

CCG  GCG  CCG  GCC  GGG  GAA  GTC  GCT  CCT  ACC  CCG  ACG  ACA  CCG  ACA  CCG    2038
Pro  Ala  Pro  Ala  Gly  Glu  Val  Ala  Pro  Thr  Pro  Thr  Thr  Pro  Thr  Pro
     305                     310                          315

CAG  CGG  ACC  TTA  CCG  GCC    T  GACC                                            2061
Gln  Arg  Thr  Leu  Pro  Ala
320                      325
```

( 2 ) INFORMATION FOR SEQ ID NO: 2:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Met  His  Gln  Val  Asp  Pro  Asn  Leu  Thr  Arg  Arg  Lys  Gly  Arg  Leu  Ala
 1                   5                    10                     15

Ala  Leu  Ala  Ile  Ala  Ala  Met  Ala  Ser  Ala  Ser  Leu  Val  Thr  Val  Ala
               20                    25                         30

Val  Pro  Ala  Thr  Ala  Asn  Ala  Asp  Pro  Glu  Pro  Ala  Pro  Pro  Val  Pro
               35                    40                         45

Thr  Thr  Ala  Ala  Ser  Pro  Pro  Ser  Thr  Ala  Ala  Ala  Pro  Pro  Ala  Pro
     50                         55                        60

Ala  Thr  Pro  Val  Ala  Pro  Pro  Pro  Ala  Ala  Ala  Asn  Thr  Pro  Asn
 65                       70                    75                          80

Ala  Gln  Pro  Gly  Asp  Pro  Asn  Ala  Ala  Pro  Pro  Ala  Asp  Pro  Asn
                    85                          90                     95

Ala  Pro  Pro  Pro  Pro  Val  Ile  Ala  Pro  Asn  Ala  Pro  Gln  Pro  Val  Arg
               100                      105                    110

Ile  Asp  Asn  Pro  Val  Gly  Gly  Phe  Ser  Phe  Ala  Leu  Pro  Ala  Gly  Trp
          115                      120                    125

Val  Glu  Ser  Asp  Ala  Ala  His  Phe  Asp  Tyr  Gly  Ser  Ala  Leu  Leu  Ser
     130                      135                    140

Lys  Thr  Thr  Gly  Asp  Pro  Phe  Pro  Gly  Gln  Pro  Pro  Pro  Val  Ala
145                      150                    155                         160

Asn  Asp  Thr  Arg  Ile  Val  Leu  Gly  Arg  Leu  Asp  Gln  Lys  Leu  Tyr  Ala
                    165                     170                    175

Ser  Ala  Glu  Ala  Thr  Asp  Ser  Lys  Ala  Ala  Ala  Arg  Leu  Gly  Ser  Asp
               180                     185                    190

Met  Gly  Glu  Phe  Tyr  Met  Pro  Tyr  Pro  Gly  Thr  Arg  Ile  Asn  Gln  Glu
          195                     200                    205

Thr  Val  Ser  Leu  Asp  Ala  Asn  Gly  Val  Ser  Gly  Ser  Ala  Ser  Tyr  Tyr
     210                     215                    220

Glu  Val  Lys  Phe  Ser  Asp  Pro  Ser  Lys  Pro  Asn  Gly  Gln  Ile  Trp  Thr
225                     230                    235                         240

Gly  Val  Ile  Gly  Ser  Pro  Ala  Ala  Asn  Ala  Pro  Asp  Ala  Gly  Pro  Pro
                    245                     250                    255

Gln  Arg  Trp  Phe  Val  Val  Trp  Leu  Gly  Thr  Ala  Asn  Asn  Pro  Val  Asp
               260                     265                    270

Lys  Gly  Ala  Ala  Lys  Ala  Leu  Ala  Glu  Ser  Ile  Arg  Pro  Leu  Val  Ala
               275                     280                    285

Pro  Pro  Pro  Ala  Pro  Ala  Pro  Ala  Pro  Ala  Glu  Pro  Ala  Pro  Ala  Pro
```

290                           295                              300
Ala Pro Ala Gly Glu Val Ala Pro Thr Pro Thr Thr Pro Thr Pro Gln
305                           310                 315                          320

Arg Thr Leu Pro Ala
                325

( 2 ) INFORMATION FOR SEQ ID NO: 3:

( i ) SEQUENCE CHARACTERISTICS:
        ( A ) LENGTH: 286 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( x i ) SEQUENCE DESCRIPTION: SEQ ID NO: 3:

Asp Pro Glu Pro Ala Pro Pro Val Pro Thr Ala Ala Ser Pro Pro
1               5                   10                  15

Ser Thr Ala Ala Ala Pro Pro Ala Pro Ala Thr Pro Val Ala Pro Pro
            20                  25                  30

Pro Pro Ala Ala Ala Asn Thr Pro Asn Ala Gln Pro Gly Asp Pro Asn
            35                  40                  45

Ala Ala Pro Pro Pro Ala Asp Pro Asn Ala Pro Pro Pro Val Ile
    50                  55                  60

Ala Pro Asn Ala Pro Gln Pro Val Arg Ile Asp Asn Pro Val Gly Gly
65                  70                  75                      80

Phe Ser Phe Ala Leu Pro Ala Gly Trp Val Glu Ser Asp Ala Ala His
                85                  90                  95

Phe Asp Tyr Gly Ser Ala Leu Leu Ser Lys Thr Thr Gly Asp Pro Pro
            100                 105                 110

Phe Pro Gly Gln Pro Pro Pro Val Ala Asn Asp Thr Arg Ile Val Leu
            115                 120                 125

Gly Arg Leu Asp Gln Lys Leu Tyr Ala Ser Ala Glu Ala Thr Asp Ser
    130                 135                 140

Lys Ala Ala Ala Arg Leu Gly Ser Asp Met Gly Glu Phe Tyr Met Pro
145                 150                 155                 160

Tyr Pro Gly Thr Arg Ile Asn Gln Glu Thr Val Ser Leu Asp Ala Asn
                165                 170                 175

Gly Val Ser Gly Ser Ala Ser Tyr Tyr Glu Val Lys Phe Ser Asp Pro
            180                 185                 190

Ser Lys Pro Asn Gly Gln Ile Trp Thr Gly Val Ile Gly Ser Pro Ala
    195                 200                 205

Ala Asn Ala Pro Asp Ala Gly Pro Pro Gln Arg Trp Phe Val Val Trp
    210                 215                 220

Leu Gly Thr Ala Asn Asn Pro Val Asp Lys Gly Ala Ala Lys Ala Leu
225                 230                 235                 240

Ala Glu Ser Ile Arg Pro Leu Val Ala Pro Pro Ala Pro Ala Pro
                245                 250                 255

Ala Pro Ala Glu Pro Ala Pro Ala Pro Ala Pro Ala Gly Glu Val Ala
            260                 265                 270

Pro Thr Pro Thr Thr Pro Thr Pro Gln Arg Thr Leu Pro Ala
        275                 280                 285